United States Patent
Shioi

(10) Patent No.: US 7,684,841 B2
(45) Date of Patent: Mar. 23, 2010

(54) LIVING BODY INGREDIENT CONCENTRATION MEASURING INSTRUMENT

(75) Inventor: Masahiko Shioi, Osaka (JP)

(73) Assignee: Panasonic Corporation, Kadoma (JP)

( * ) Notice: Subject to any disclaimer, the term of this patent is extended or adjusted under 35 U.S.C. 154(b) by 328 days.

(21) Appl. No.: 11/915,889

(22) PCT Filed: Mar. 8, 2007

(86) PCT No.: PCT/JP2007/054538

§ 371 (c)(1),
(2), (4) Date: Nov. 29, 2007

(87) PCT Pub. No.: WO2007/105588

PCT Pub. Date: Sep. 20, 2007

(65) Prior Publication Data

US 2009/0316137 A1 Dec. 24, 2009

(30) Foreign Application Priority Data

Mar. 10, 2006 (JP) ............................. 2006-065366

(51) Int. Cl.
*A61B 5/1455* (2006.01)
(52) U.S. Cl. ...................................... 600/310; 600/316
(58) Field of Classification Search ................ 600/310, 600/316, 322, 341, 473
See application file for complete search history.

(56) References Cited

U.S. PATENT DOCUMENTS

| | | |
|---|---|---|
| 5,115,133 A | 5/1992 | Knudson |
| 5,515,847 A | 5/1996 | Braig et al. |
| 5,666,956 A | 9/1997 | Buchert |
| 5,823,966 A | 10/1998 | Buchert |
| 6,002,953 A | 12/1999 | Block |
| 6,424,851 B1 | 7/2002 | Berman et al. |
| 2004/0199060 A1 | 10/2004 | Oshima et al. |

(Continued)

FOREIGN PATENT DOCUMENTS

EP 1 941 834 A1 7/2007

(Continued)

OTHER PUBLICATIONS

International Search Report for corresponding Application No. PCT/JP2007/054538 dated Apr. 10, 2007.

(Continued)

*Primary Examiner*—Eric F Winakur
(74) *Attorney, Agent, or Firm*—Renner, Otto, Boisselle & Sklar, LLP

(57) ABSTRACT

A device for measuring the concentration of a biological constituent based on infrared radiation emitted by a subject's eardrum with the influence of the eardrum's thickness taken into account is provided.

The biological constituent concentration measuring device includes: a detecting section for detecting infrared radiation emitted by an eardrum; an acquisition section for acquiring thickness information about the thickness of the eardrum; and a computing section for figuring out the concentration of the biological constituent based on the infrared radiation detected and the thickness information acquired. The infrared radiation emitted by the eardrum is subject to the influence of the subject's eardrum thickness. Therefore, by calculating the biological constituent concentration based on not only the infrared radiation detected but also the eardrum thickness information, the biological constituent concentration can be measured highly accurately.

16 Claims, 13 Drawing Sheets

U.S. PATENT DOCUMENTS

| | | |
|---|---|---|
| 2004/0220457 A1 | 11/2004 | Burd et al. |
| 2004/0220458 A1 | 11/2004 | Burd et al. |
| 2005/0043630 A1 | 2/2005 | Buchert |
| 2005/0085701 A1 | 4/2005 | Burd et al. |
| 2005/0209514 A1 | 9/2005 | Oshima et al. |
| 2006/0041195 A1 | 2/2006 | Shioi et al. |

FOREIGN PATENT DOCUMENTS

| | | |
|---|---|---|
| EP | 1 955 652 A1 | 8/2008 |
| JP | 2001-503999 | 3/2001 |
| JP | 2001-506164 | 5/2001 |
| JP | 2002-513604 | 5/2002 |
| JP | 2005-188999 | 7/2005 |
| JP | 2006-296660 | 11/2006 |
| JP | 2007-144103 | 6/2007 |

OTHER PUBLICATIONS

C. D. Malchoff et al., "A Novel Noninvasive Blood Glucose Monitor", Diabetes Care, Dec. 2002, vol. 25, No. 12, pp. 2268-2275.

J. M. Buchert, "Thermal Emission Spectroscopy as a Tool for Non-Invasive Blood Glucose Measurements", Proceedings of the SPIE, vol. 5566, No. 1, 2004, pp. 100-111.

Supplementary European Search Report issued on Sep. 16, 2008 for a corresponding European Patent Application No. 07738029.3.

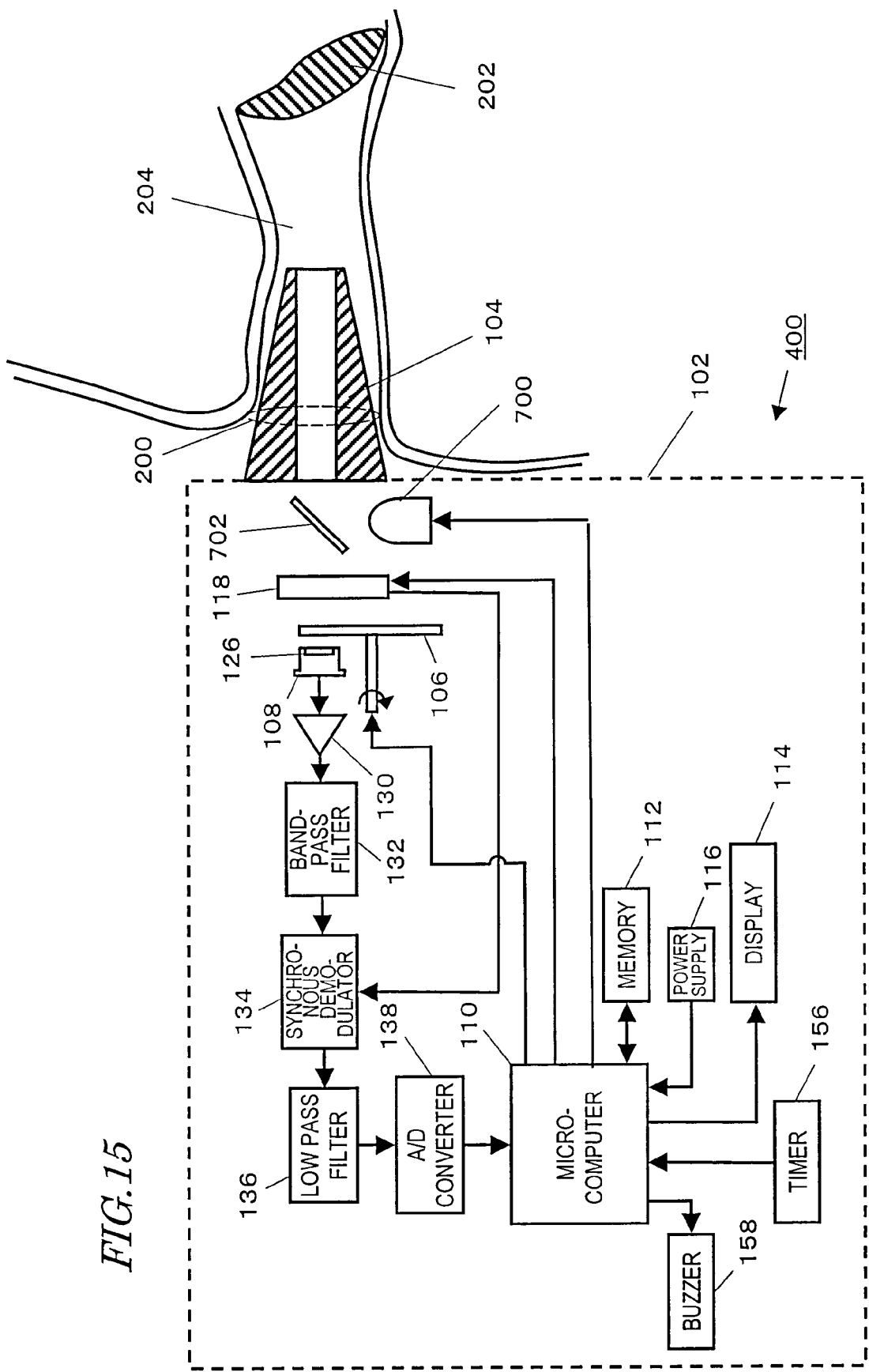

LIVING BODY INGREDIENT CONCENTRATION MEASURING INSTRUMENT

TECHNICAL FIELD

The present invention relates to a biological constituent concentration measuring device for making non-invasive monitoring on biological information using infrared radiation emitted by an organism.

BACKGROUND ART

A biological constituent concentration measuring device for determining the blood glucose non-invasively by the infrared radiation that has come from an organism (e.g., an eardrum among other things) has been proposed. For example, Patent Document No. 1 discloses an apparatus for measuring a blood glucose level in a human body tissue by making a non-invasive analysis on a radiation spectral line, which is characteristic of the human body tissue and included in the infrared radiation that has been emitted naturally as heat from his or her eardrum.

According to the Planck radiation formula, however, the intensity of the infrared radiation emitted as thermal radiation from an object varies with the temperature of the object that produces the infrared radiation. The temperature of the eardrum changes with the body temperature. For that reason, the eardrum temperature could change from one person to another or every time the measurement is done. Due to such a variation in eardrum temperature, the blood glucose levels that have been measured based on the infrared radiation emitted by the eardrum may also vary.

That is why it has been proposed that such an apparatus for measuring the blood glucose level non-invasively using the infrared radiation emitted by the eardrum should correct the influence of the eardrum temperature on the infrared radiation given out from the eardrum. For example, Patent Document No. 2 discloses a technique for correcting the influence of the temperature on the radiation spectral line by measuring the temperature inside the acoustic foramen. More specifically, the ear temperature is detected by measuring the intensity of the infrared radiation in a broad wavelength range of 8 µm to 14 µm.

Patent Document No. 1: U.S. Pat. No. 5,666,956 (its entire description and all drawings)

Patent Document No. 2: United States Patent Application Publication Ser. No. 2005/0043630 (its entire description and all drawings)

DISCLOSURE OF INVENTION

Problems to be Solved by the Invention

However, the present inventors discovered that the intensity of the infrared radiation emitted by an eardrum was affected by not only the eardrum temperature but also the thickness of the eardrum. According to this discovery, the concentration of a biological constituent (e.g., a blood glucose level) cannot be measured accurately based on the intensity of the infrared radiation unless not just the eardrum temperature but also its thickness are considered.

The apparatus disclosed in Patent Document No. 2, however, pays no attention to the influence of the eardrum thickness on the infrared radiation emitted by the eardrum. That is why the biological constituent concentration measured by that apparatus is far from being sufficiently accurate.

In order to overcome the problems described above, the present invention has an object of providing a biological constituent concentration measuring device that can measure the biological constituent concentration accurately by correcting the influence of the eardrum thickness on the infrared radiation emitted by the eardrum.

Means for Solving the Problems

A device for measuring the concentration of a biological constituent according to the present invention includes: a detecting section for detecting infrared radiation emitted by an eardrum; an acquisition section for acquiring thickness information about the thickness of the eardrum; and a computing section for figuring out the concentration of the biological constituent based on the infrared radiation detected and the thickness information acquired.

On receiving infrared radiation falling within a wavelength range A1, including the wavelength of infrared radiation absorbed into the biological constituent, the detecting section may output a signal A1 representing the intensity of the infrared radiation. On receiving infrared radiation falling within a wavelength range B, which is selected from a wavelength range that is equal to or longer than 11 µm, the detecting section may output a signal B representing the intensity of the infrared radiation. On receiving an infrared radiation falling within a wavelength range C, which is selected from the wavelength range of 4.5 µm to 5.8 µm, the detecting section may output a signal C representing the intensity of the infrared radiation. And the computing section may figure out the concentration of the biological constituent based on the signals A1, B and C that have been supplied from the detecting section.

On receiving an infrared radiation that falls within a wavelength range A2, in which the infrared radiation is absorbed into the biological constituent less than the infrared radiation falling within the wavelength range A1, and that is absorbed into a different biological constituent than the biological constituent, the detecting section may output a signal A2 representing the intensity of the infrared radiation. And the computing section may figure out the concentration of the biological constituent based on the signals A1, A2, B and C that have been supplied from the detecting section.

The measuring device may further include a storage section for storing concentration correlation data showing a correlation between respective signal values of the detecting section about the wavelength ranges A1, B and C and the concentration of the biological constituent. The computing section may figure out the concentration of the biological constituent by making reference to the correlation data with the signals A1, B and C that have been supplied from the detecting section.

The storage section may further store temperature correlation data showing a correlation between the signal value of the detecting section about the wavelength range B and a temperature and thickness correlation data showing a correlation between the temperature and the signal value of the detecting section about the wavelength range C, and the thickness of the eardrum. The acquisition section may determine the temperature by reference to the temperature correlation data with the signal B supplied from the detecting section and then acquire the thickness information by reference to the thickness correlation data with the temperature determined and the signal C supplied from the detecting section.

The computing section may make reference to the concentration correlation data with the temperature determined, the thickness information acquired, and the signal value of the detecting section about the wavelength range A1, thereby calculating the concentration of the biological constituent.

The measuring device may further include at least three optical elements that are arranged on an optical path between the eardrum and the detecting section. The optical elements may include an optical element that transmits the infrared radiation falling within the wavelength range A1, an optical element that transmits the infrared radiation falling within the wavelength range B, and an optical element that transmits the infrared radiation falling within the wavelength range C.

The measuring device may further include: a light source for emitting light; a lens for condensing the light that has been emitted from the light source and then reflected from the eardrum; an actuator for moving the lens; a spatial filter; and a photodetector for detecting a portion of the light that has been condensed by the lens and then transmitted through the spatial filter and outputting a signal representing the intensity of the light. The acquisition section may monitor the levels of the output signal of the photodetector with the lens moved, and calculate, as the thickness information, a distance that the lens travels from a first position where the output signal of the photodetector shows a first local maximum value to a second position where the output signal of the photodetector shows a second local maximum value.

The measuring device may further include: a light source for emitting light; an optical system for converging the light onto the eardrum; and a photodetector for detecting the light that has been reflected from the eardrum. The acquisition section may figure out the thickness information based on a first setting of the optical system when the light emitted from the light source is focused on a first side of the eardrum and a second setting of the optical system when the light emitted from the light source is focused on a second side of the eardrum.

The light source may be a laser radiation source that emits a laser beam with a wavelength falling within the range of 400 nm to 420 nm.

On receiving an infrared radiation falling within a wavelength range A1, including the wavelength of an infrared radiation absorbed into the biological constituent, the detecting section may output a signal A1 representing the intensity of the infrared radiation. On receiving an infrared radiation falling within a wavelength range B, which is equal to or longer than 11 μm, the detecting section may output a signal B representing the intensity of the infrared radiation. And the computing section may figure out the concentration of the biological constituent based on the signals A1 and B that have been supplied from the detecting section.

The measuring device may further include a storage section for storing correlation data showing a correlation between respective signal values of the detecting section about the wavelength ranges A1 and B, the thickness information, and the concentration of the biological constituent. And the computing section may figure out the concentration of the biological constituent by reference to the correlation data with the signals A1 and B that have been supplied from the detecting section and with the thickness information.

The measuring device may further include an infrared radiation source for increasing the intensity of the infrared radiation that has come from the eardrum. The detecting section may output a signal representing the intensity of the infrared radiation received.

The acquisition section may acquire the thickness information over a network.

The acquisition section may acquire the thickness information by way of a removable storage medium.

The measuring device may further include an output section for outputting information about the biological constituent concentration calculated.

EFFECTS OF THE INVENTION

A biological constituent concentration measuring device according to the present invention figures out the concentration of a biological constituent based on the infrared radiation emitted by an eardrum and thickness information about the thickness of the eardrum. The thickness information represents the thickness of the eardrum. And the measuring device calculates the concentration of the biological constituent based on the intensity of the infrared radiation emitted by the eardrum and with the thickness taken into account. In this manner, the concentration of the biological constituent can be measured highly accurately.

BRIEF DESCRIPTION OF DRAWINGS

FIG. 15 shows the hardware configuration of the measuring device 400 of the third preferred embodiment.

DESCRIPTION OF REFERENCE NUMERALS

Figure 1:
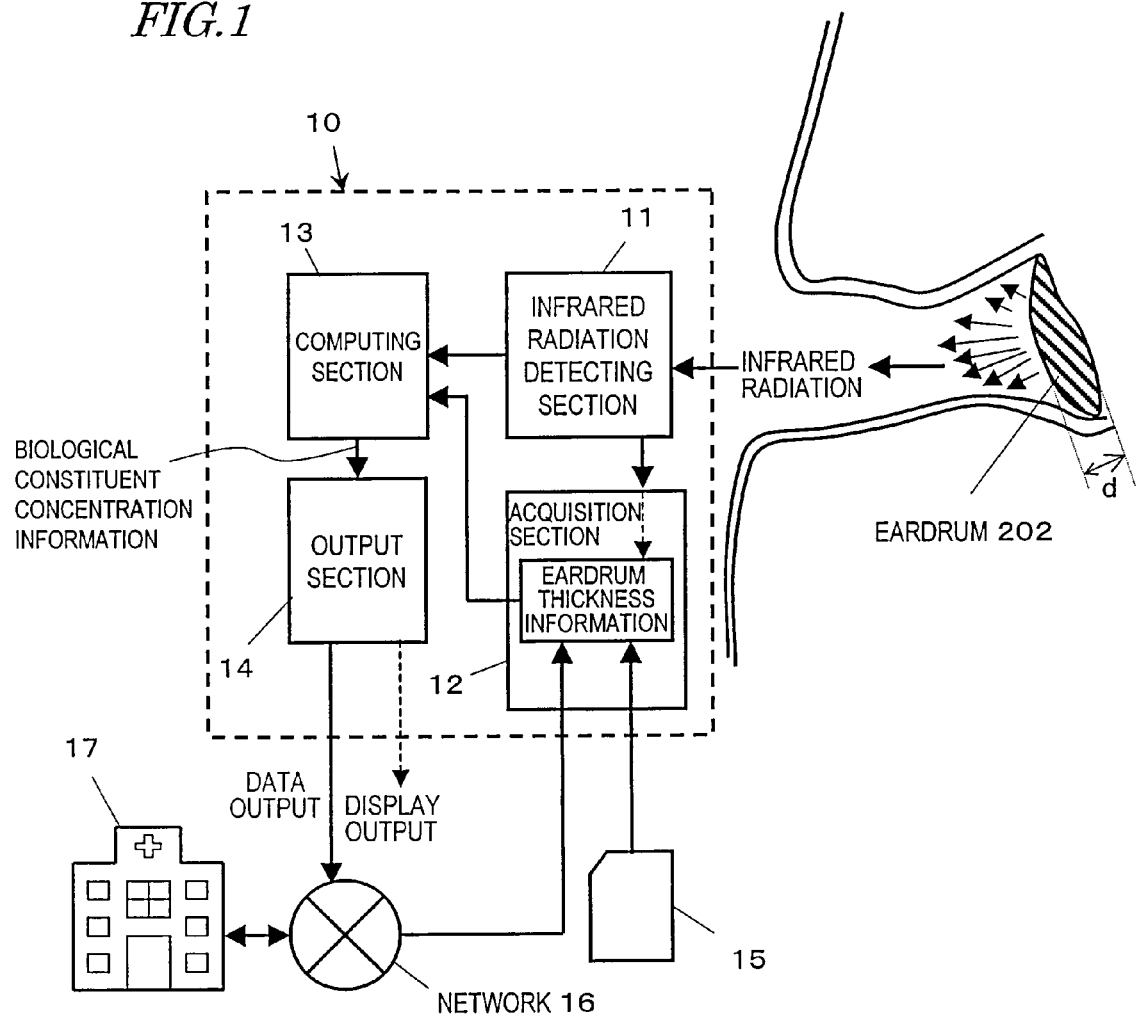
FIG. 1 shows an arrangement of functional blocks in a biological constituent concentration measuring device 10 according to the present invention.

10, 100, 300, 400 biological constituent concentration measuring device
11 infrared radiation detecting section
12 acquisition section
13 computing section
14 output section
15 memory card
16 network
17 hospital
101 power switch
102, 302 body
103 measuring start switch
104 waveguide
106, 306 optical filter wheel
108 infrared sensor
110 microcomputer
112 memory
114 display
116 power supply
118 chopper
121 first optical filter
122 second optical filter
123 third optical filter
124 fourth optical filter
125 shaft
126 sensing area
127 ring
130 pre-amplifier
132 band-pass filter
134 synchronous demodulator
136 low pass filter
138 A/D converter
142 first half mirror
144 second half mirror
156 timer
158 buzzer
200 acoustic foramen
202 ear drum
204 ear canal
310 light source
312 first condenser lens
314 second condenser lens
316 actuator
318 spatial filter
320 photodetector
322 lens frame
700 infrared radiation source
702 half mirror

BEST MODE FOR CARRYING OUT THE INVENTION

If the infrared radiation emitted by an organism is measured, information about a biological constituent concentration such as a blood glucose level can be obtained. Hereinafter, that principle will be illustrated first, and then the functional block arrangement of a biological constituent concentration measuring device according to the present invention, operating on that principle, will be described. After that, first through third specific preferred embodiments of a biological constituent concentration measuring device according to the present invention will be set forth.

The radiation energy W of the infrared radiation that has been emitted as thermal radiation from an organism is represented by the following Equations (1) and (2):

$$W = S \int_{\lambda_1}^{\lambda_2} \varepsilon(\lambda) \cdot W_0(T, \lambda) d\lambda(W) \tag{1}$$

$$W_0(\lambda, T) = 2hc^2 \{\lambda^5 \cdot [\exp(hc/\lambda kT) - 1]\}^{-1} (W/cm^2 \cdot \mu m) \tag{2}$$

where W is the radiation energy of the infrared radiation that has been emitted as thermal radiation from an organism, $\varepsilon(\lambda)$ is the emissivity of the organism at a wavelength $\lambda$, $W_0(\lambda, T)$ is the spectral radiant density of a thermal radiation from blackbody at the wavelength $\lambda$ and a temperature T, h is Planck's constant (where $h=6.625\times10^{-34}$ W·S$^2$)), c is the velocity of light (where $c=2.998\times10^{10}$ cm/s), $\lambda_1$ and $\lambda_2$ are wavelengths (μm) of infrared radiations emitted as thermal radiations from the organism, T is the temperature (K) of the organism, S is the detection area (cm$^2$) and k is Boltzmann constant.

According to Equation (1), if the detection area S is constant, the radiation energy W of the infrared radiation emitted as a thermal radiation from an organism depends on the emissivity $\varepsilon(\lambda)$ of the organism at a wavelength $\lambda$. According to the Kirchhoff's law on radiation, the emissivity and the absorptivity are equal to each other at the same temperature and at the same wavelength.

$$\varepsilon(\lambda) = \alpha(\lambda) \tag{3}$$

where $\alpha(\lambda)$ is the absorptivity of the organism at the wavelength $\lambda$.

That is why it can be seen that when the emissivity needs to be obtained, the absorptivity may be calculated. Based on the principle of energy conservation, the absorptivity, the transmittance and the reflectance satisfy the following Equation (4):

$$\alpha(\lambda) + r(\lambda) + t(\lambda) = 1 \tag{4}$$

where $r(\lambda)$ is the reflectance of the organism at the wavelength $\lambda$ and $t(\lambda)$ is the transmittance of the organism at the wavelength $\lambda$.

Therefore, the emissivity can be calculated by the following Equation (5) using the transmittance and the reflectance:

$$\varepsilon(\lambda) = \alpha(\lambda) = 1 - r(\lambda) - t(\lambda) \tag{5}$$

The transmittance is represented as the ratio of the intensity of the light that has been transmitted through an object of interest to that of the incoming light. The intensity of the incoming light and that of the light that has been transmitted through the object of interest are given by the Lambert-Beer law:

$$I_t(\lambda) = I_0(\lambda) \exp\left(-\frac{4\pi k(\lambda)}{\lambda} d\right) \tag{6}$$

where $I_t$ is the intensity of the transmitted light, $I_0$ is the intensity of the incoming light, d is the thickness of the organism and $k(\lambda)$ is the extinction coefficient of the organism at the wavelength $\lambda$. The extinction coefficient of the organism represents absorption of the light into the organism.

Consequently, the transmittance is given by the following Equation (7):

$$t(\lambda) = \exp\left(-\frac{4\pi k(\lambda)}{\lambda}d\right) \quad (7)$$

Next, the reflectance will be described. The reflectance should be calculated as the average of reflectances in all directions. In this example, only the reflectance to perpendicularly incident light will be considered for the sake of simplicity. Supposing the refractive index of the air is one, the reflectance to the perpendicularly incident light is given by the following Equation (8):

$$r(\lambda) = \frac{(n(\lambda) - 1)^2 + k^2(\lambda)}{(n(\lambda) + 1)^2 + k^2(\lambda)} \quad (8)$$

where $n(\lambda)$ is the refractive index of the organism at the wavelength $\lambda$.

Consequently, the emissivity is given by the following Equation (9):

$$\varepsilon(\lambda) = 1 - r(\lambda) - t(\lambda) \quad (9)$$
$$= 1 - \frac{(n(\lambda) - 1)^2 + k(\lambda)^2}{(n(\lambda) + 1)^2 + k(\lambda)^2} - \exp\left(-\frac{4\pi k(\lambda)}{\lambda}d\right)$$

If the concentration of a constituent varies in an organism, the refractive index and the extinction coefficient of the organism will also change. The reflectance is usually as low as about 0.03 in the infrared range. Also, as can be seen from Equation (8), the reflectance does not depend on the refractive index or the extinction coefficient so much. That is why even if the refractive index and the extinction coefficient change due to a variation in biological constituent concentration, the reflectance will vary a little.

On the other hand, the transmittance heavily depends on the extinction coefficient as can be seen from Equation (7). For that reason, if the extinction coefficient of an organism (i.e., the degree of absorption of light into the organism) changes due to a variation in biological constituent concentration, the transmittance will change, too.

Thus, it can be seen that the radiation energy of the infrared radiation emitted as a thermal radiation from an organism depends on the concentration of the biological constituent. That is to say, the biological constituent concentration can be calculated based on the intensity of the radiation energy of the infrared radiation that has been emitted as a thermal radiation from the organism.

According to Equation (7), the transmittance depends on the thickness of the vital tissue. That is to say, the smaller the thickness of the vital tissue, the more significantly the transmittance will change with a variation in the extinction coefficient of the organism and the more easily the variation in biological constituent concentration can be detected.

The eardrum has such a small thickness of about 60 μm to about 100 μm as to be suitable for determining the biological constituent concentration using infrared radiation.

The transmittance depends on the thickness of the vital tissue, and therefore, the radiation energy of the infrared radiation that has been emitted as a thermal radiation from the organism is also affected by the thickness of the vital tissue. That is why if the biological constituent concentration is measured based on the infrared radiation that has been emitted as a thermal radiation from the eardrum, then the detected radiation energy of the infrared radiation emitted as the thermal radiation from the eardrum may be corrected with the thickness of the eardrum and the corrected radiation energy intensity may be converted into a biological constituent concentration value. Then, the measurement can be done more accurately.

Also, according to Equations (1) and (2), the spectral radiant density of a thermal radiation from the blackbody depends on the temperature of the vital tissue, and therefore, the radiation energy of the infrared radiation that has been emitted as a thermal radiation from the organism is also affected by the temperature of the vital tissue. That is why if the biological constituent concentration is measured based on the infrared radiation that has come from the eardrum, then the detected radiation energy of the infrared radiation emitted by the eardrum may be corrected with the temperature of the eardrum and the corrected radiation energy intensity may be converted into a biological constituent concentration value. Then, the measurement can be done more accurately.

Next, the functional block arrangement of a biological constituent concentration measuring device according to the present invention, which operates on the principle described above, will be described with reference to FIG. 1.

FIG. 1 shows an arrangement of functional blocks in a biological constituent concentration measuring device 10 according to the present invention. The measuring device 10 includes an infrared radiation detecting section 11, an acquisition section 12, a computing section 13 and an output section 14.

The biological constituent concentration measuring device 10 (which will be simply referred to herein as a "measuring device 10") not only detects the infrared radiation that has come from the eardrum 202 but also acquires information representing the thickness d of the eardrum 202 (which will be referred to herein as "eardrum thickness information"), thereby calculating the concentration of the biological constituent based on these data collected. Then, the measuring device 10 displays information about the biological constituent concentration thus calculated on a monitor, writes it on a memory card, and/or transmits it to a hospital connected to the network. As used herein, the "biological constituent concentration" is at least one of a glucose concentration (i.e., a blood glucose level), a hemoglobin concentration, a cholesterol concentration and a fat concentration.

These components function as follows.

The infrared radiation detecting section 11 receives the infrared radiation that has come from the eardrum 202 and detects infrared radiation falling within a predetermined wavelength range.

The acquisition section 12 acquires eardrum thickness information representing the thickness d of the eardrum 202. This information can be acquired by a measuring process that uses either the infrared radiation emitted by the eardrum 202 or a laser beam. This measuring process will be described in detail later with respect to first through third preferred embodiments of the present invention.

If the thickness of the eardrum 202 of a subject has already been measured and if the eardrum thickness information has already been stored outside of the measuring device 10, the acquisition section 12 may acquire that eardrum thickness information from outside of the measuring device 10. For example, if the eardrum thickness information is stored in a memory card 15 that is attachable and removable to/from the measuring device 10, then the eardrum thickness information may be read from the memory card 15 that is loaded in the measuring device 10. On the other hand, if the eardrum thickness information is managed in a hospital 17, for example, then the eardrum thickness information may also be retrieved from the hospital 17 over a network 16.

The computing section 13 calculates the biological constituent concentration based on the infrared radiation detected by the infrared radiation detecting section 11 and on the eardrum thickness information. The computing section 13 figures out the biological constituent concentration (such as a blood glucose level) based on the eardrum thickness information that represents the thickness of the eardrum. As a result, the concentration can be measured accurately. Specific processing by the computing section 13 will be described in detail later for the first through third preferred embodiments of the present invention.

The output section 14 displays, on a monitor, the information about the biological constituent concentration calculated by the computing section 13, writes it on the memory card 15, and/or transmits it to the hospital 17 connected to the network 16. Optionally, besides or instead of displaying the information on the monitor, the information representing the biological constituent concentration may also be output as audio through a loudspeaker.

Hereinafter, first through third preferred embodiments of a measuring device 10 according to the present invention will be described with reference to the accompanying drawings.

Embodiment 1

Figure 2:
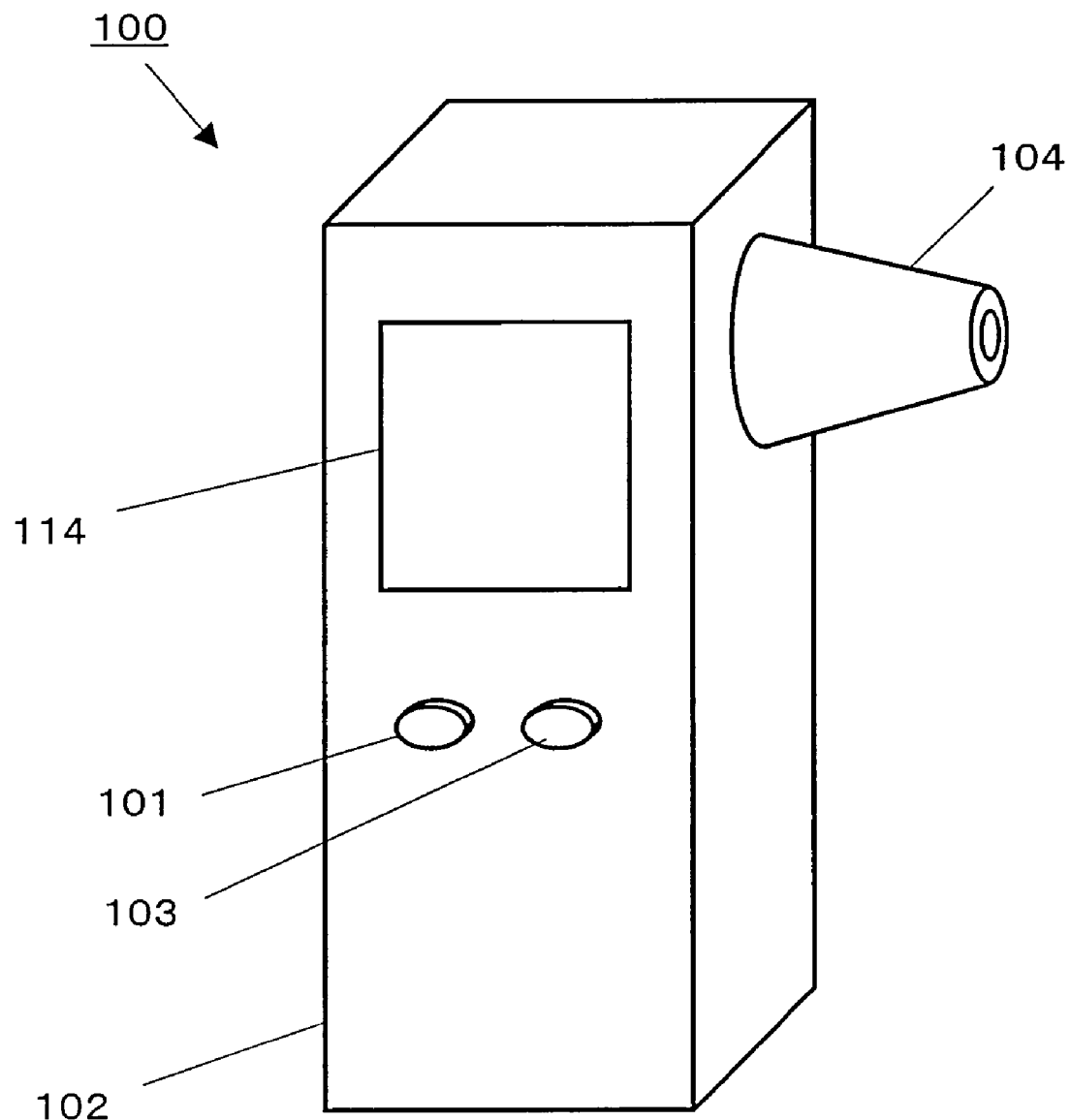
FIG. 2 is a perspective view illustrating the appearance of a biological constituent concentration measuring device 100 according to a first specific preferred embodiment of the present invention.

FIG. 2 is a perspective view illustrating the appearance of a biological constituent concentration measuring device 100 according to a first specific preferred embodiment of the present invention.

The biological constituent concentration measuring device 100 (which will be simply referred to herein as a "measuring device 100") includes a body 102 and a waveguide 104 arranged on a side surface of the body 102. The body 102 includes a display 114 to show the biological constituent concentration measured, a switch 101 to turn ON and OFF the measuring device 100, and another switch 103 to start the measuring process.

The display 114 may be an liquid crystal display or an organic electroluminescent (EL) display, for example. The display 114 corresponds to the output section 14 shown in FIG. 1.

The waveguide is inserted into the acoustic foramen and has the function of guiding the infrared radiation, coming from the eardrum, into the measuring device 100. Anything may be used as the waveguide as long as it can guide infrared radiation. For example, a hollow tube or an optical fiber that transmits infrared radiation may be used. If a hollow tube is used, the inner surface of the hollow tube is preferably coated with a gold layer, which may be formed by either plating the inner surface of the hollow tube with gold or evaporating and depositing gold on that surface.

Next, the hardware configuration of the measuring device 100 will be described with reference to FIGS. 3 and 4.

Figure 3:
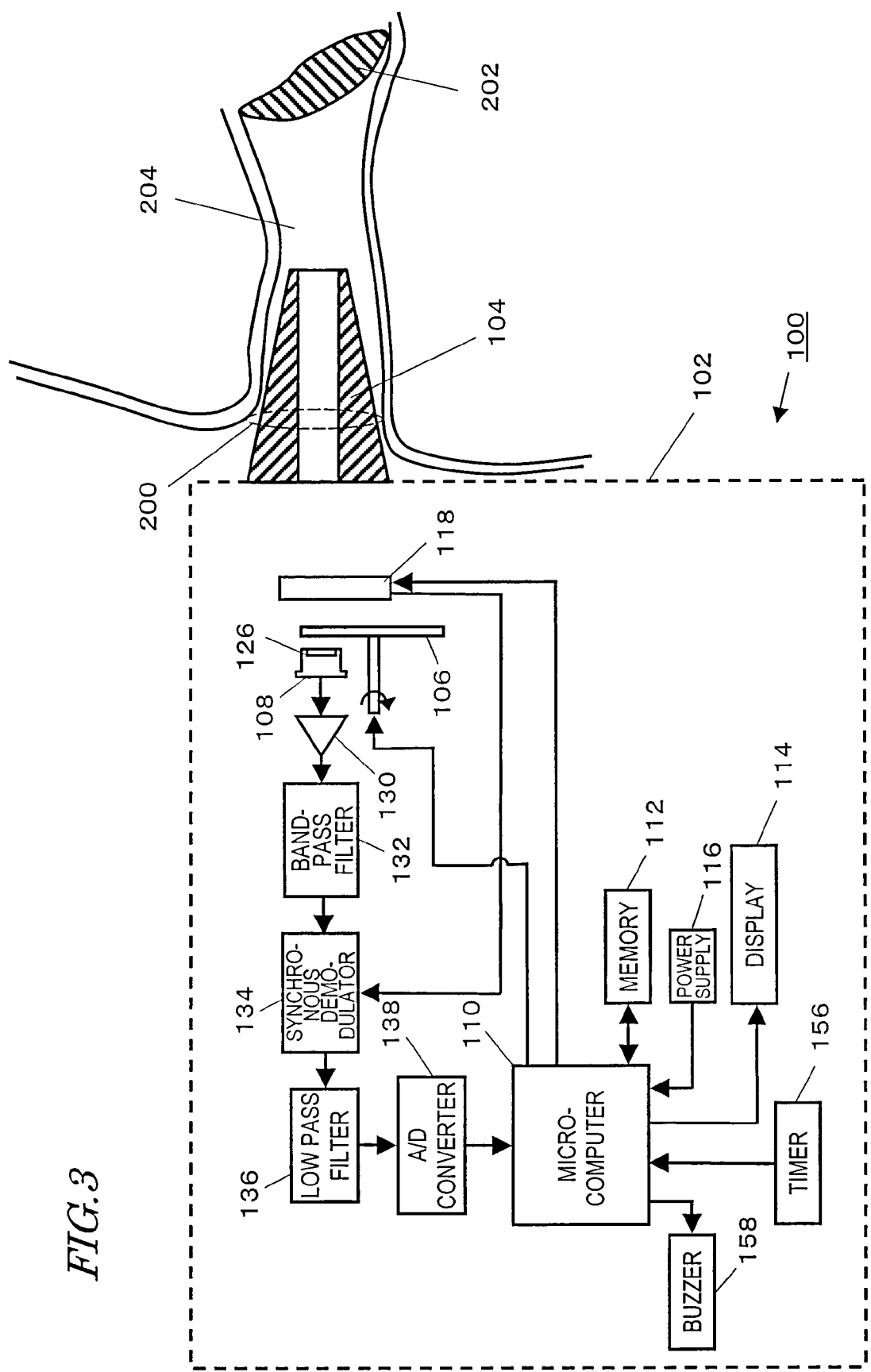
FIG. 3 shows the hardware configuration of the measuring device 100.

FIG. 3 shows the hardware configuration of the measuring device 100.

The body of the measuring device 100 includes a chopper 118, an optical filter wheel 106, an infrared sensor 108, a pre-amplifier 130, a band-pass filter 132, a synchronous demodulator 134, a low pass filter 136, an analog-to-digital (A/D) converter 138, a microcomputer 110, a memory 112, a display 114, a power supply 116, a timer 156 and a buzzer 158.

Among these components of the measuring device 100, the infrared sensor 108, the pre-amplifier 130, the band-pass filter 132, the synchronous demodulator 134, the low pass filter 136, and the A/D converter 138 together function as the infrared radiation detecting section 11 of the measuring device 10 shown in FIG. 1. The microcomputer 110 and the memory 112 function as the acquisition section 12 and the computing section 13 shown in FIG. 1. And the output section 14 functions as the display 114.

In the measuring device 100, the infrared sensor 108 detects the infrared radiation that has come from the eardrum. As used herein, the "infrared radiation emitted by the eardrum" includes an infrared radiation radiated from the eardrum as a thermal radiation from the eardrum itself and an infrared ray that has been radiated toward, and then reflected from, the eardrum. Unlike a measuring device according to the third preferred embodiment of the present invention to be described later, the measuring device 100 of this preferred embodiment has no light source that radiates infrared radiation. That is why the infrared sensor 108 of this preferred embodiment detects only the infrared radiation that has been radiated as a thermal radiation from the eardrum itself.

Any sensor may be used as the infrared sensor as long as the sensor can detect radiations having wavelengths falling within the infrared range of the spectrum. For example, the infrared sensor may be a pyroelectric sensor, a thermopile, a bolometer, an HgCdTe (MCT) detector or a Golay cell.

The microcomputer 110 may be a computer such as a central processing unit (CPU) or a digital signal processor (DSP).

The power supply 116 provides AC or DC power to operate the electronic circuits inside the measuring device 100. A battery is preferably used as the power supply 116.

The chopper 118 chops the infrared radiation that has been radiated from the eardrum 202 and then guided into the body 102 through the waveguide 104, thereby transforming the infrared radiation into a high-frequency infrared signal. The operation of the chopper 118 is controlled in accordance with a control signal supplied from the microcomputer 110. The infrared radiation that has been chopped by the chopper 118 soon reaches the optical filter wheel 106.

Figure 4:
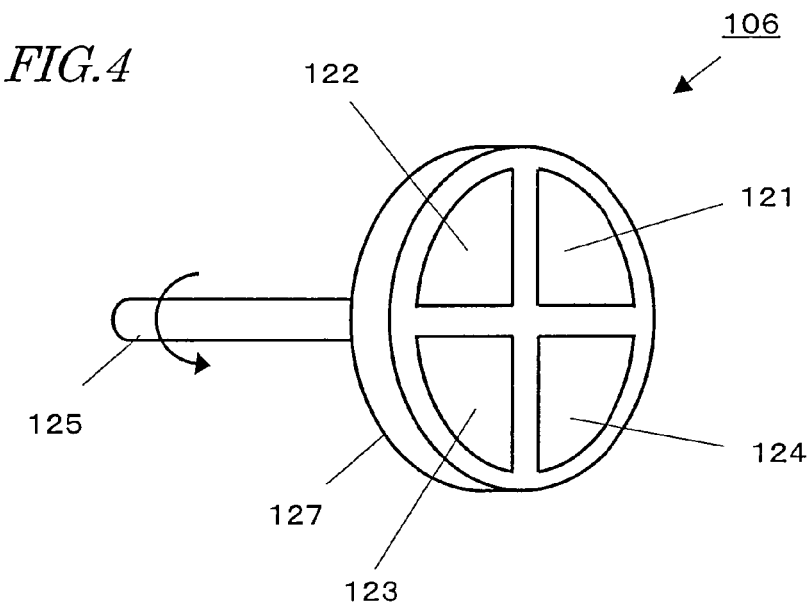
FIG. 4 is a perspective view illustrating an optical filter wheel 106 according to the first preferred embodiment.

FIG. 4 is a perspective view illustrating the optical filter wheel 106. The optical filter wheel 106 includes a first optical filter 121, a second optical filter 122, a third optical filter 123, a fourth optical filter 124 and a ring 127 to which these filters are fitted. The first through fourth optical filters 121 through 124 function as spectral filters. The wavelength ranges of infrared radiation to be transmitted through these filters will be described later.

In the example illustrated in FIG. 4, the first through fourth optical filters 122 through 124, all of which are fan-shaped, are fitted into the ring 127, thereby forming a disklike member. And at the center of that disklike member, arranged is a shaft 125. By rotating the shaft 125 in the direction pointed by the arrow shown in FIG. 4, the optical filters to pass the infrared radiation that has been chopped by the chopper 118 may be switched from one of the four optical filters 121, 122, 123 and 124 into another.

The rotation of the shaft 125 is controlled by the microcomputer 110. The control signal supplied from the microcomputer 110 is sent to a motor (not shown), which spins the shaft 125 at a number of revolutions as defined by the control signal. The shaft 125 preferably has its revolution synchronized with the rotation of the chopper 118 and is preferably controlled so as to turn 90 degrees while the chopper 118 is closed. This is because when the chopper 118 is opened next time, the infrared radiation to be chopped by the chopper 118 may be transmitted through the next optical filter.

The infrared radiation that has been transmitted through the first, second, third or fourth optical filter 121, 122, 123 or 124 reaches the infrared sensor 108 with a sensing area 126.

On reaching the infrared sensor 108, the infrared radiation is incident on the sensing area 126. The infrared sensor 108 receives the infrared radiation and transforms the infrared radiation into an electrical signal representing its intensity.

The electrical signal is output from the infrared sensor 108 to the pre-amplifier 130 and then amplified there. Then, the amplified electrical signal has its signal components filtered out by the band-pass filter 132 except those falling within a frequency range, of which the center frequency is defined by the chopping frequency. As a result, noise caused by some statistical fluctuation such as thermal noise can be minimized.

The electrical signal that has been subjected to the filtering process by the band-pass filter 132 is synchronized with the chopping frequency of the chopper 118 and integrated by the synchronous demodulator 134 so as to be demodulated into a DC signal.

Next, the electrical signal that has been demodulated by the synchronous demodulator 134 has its high frequency components filtered out by the low pass filter 136. In this manner, its noise can be further reduced.

Subsequently, the electrical signal that has been subjected to the filtering process by the low pass filter 136 is converted by the A/D converter 138 into a digital signal, which is then input to the microcomputer 110. In this case, the electrical signal that has come from any of the optical filters by way of the infrared detector 108 can have its source identified (i.e., it is possible to determine which of those optical filters the infrared radiation, represented by the electrical signal, has been transmitted through) by using a control signal for the shaft 125 as a trigger. The duration of an electrical signal associated with the same optical filter is defined as an interval after the microcomputer has output a control signal for the shaft 125 and before it outputs the next shaft control signal. By calculating the integral of the electrical signals associated with the respective optical filters on the memory 112 and then working out its average, the noise can be further reduced. That is why the measured values are preferably integrated.

In the memory 112, stored is concentration correlation data that shows a correlation between the signal values of the electrical signals corresponding to the respective intensities of the infrared radiation transmitted through the first and second optical filters 121 and 122 and the biological constituent concentration. The concentration correlation data may be obtained by monitoring the output signal levels of the infrared detector for a patient with a known biological constituent concentration (e.g., a blood glucose level) and by analyzing the correlation between the resultant output signal of the infrared detector and the biological constituent concentration.

The microcomputer 110 reads this concentration correlation data from the memory 112, calculates a digital signal per unit time based on the digital signal that has been stored in the memory 112 by reference to the concentration correlation data, and converts the digital signal into a biological constituent concentration. The memory 112 functions as a storage section such as a RAM or a ROM.

Then, the biological constituent concentration that has been worked out by the microcomputer 110 is output to and presented on the display 114.

Next, the structures of the first, second, third and fourth optical filters 121, 122, 123 and 124 and methods for correcting the temperature and thickness of the eardrum will be described.

The first optical filter 121 has such a spectral characteristic as to transmit infrared radiation that falls within a wavelength range including the wavelength to be absorbed into the biological constituent under measurement (which will be referred to herein as "measuring wavelength range").

On the other hand, the second optical filter 122 has a different spectral characteristic from the first optical filter's 121. Specifically, the second optical filter 122 has such a spectral characteristic as to transmit infrared radiation that falls within a wavelength range including a wavelength to be absorbed into not the biological constituent under measurement but another biological constituent that would interfere with the measurement of the target biological constituent (which will be referred to herein as "reference wavelength range"). In this case, that another biological constituent may be any constituent that is included a lot in the organism other than the biological constituent under measurement.

For example, glucose has an infrared absorption spectrum with a peak of absorption around 9.6 μm. That is why if the biological constituent under measurement is glucose, the first optical filter 121 preferably has such a spectral characteristic as to transmit infrared radiation that falls within a wavelength range including 9.6 μm (e.g., 9.6±0.1 μm).

Meanwhile, protein, included a lot in an organism, would absorb infrared radiation around 8.5 μm, while glucose would not absorb infrared radiation around that wavelength. That is why the second optical filter 122 preferably has such a spectral characteristic as to transmit infrared radiation that falls within a wavelength range including 8.5 μm (e.g., 8.5±0.1 μm).

The third optical filter 123 has such a spectral characteristic as to pass a wavelength range in which the infrared radiation is not absorbed into the biological constituent under measurement and in which the intensity of the infrared radiation hardly varies with the thickness of the eardrum. And the fourth optical filter 124 has such a spectral characteristic as to pass a wavelength range in which the infrared radiation has its intensity changed with the thickness of the eardrum and is hardly absorbed into the biological constituent under measurement.

Hereinafter, preferred spectral characteristics of the third and fourth optical filters 123 and 124 will be described with reference to FIGS. 5 and 6.

Figure 5:
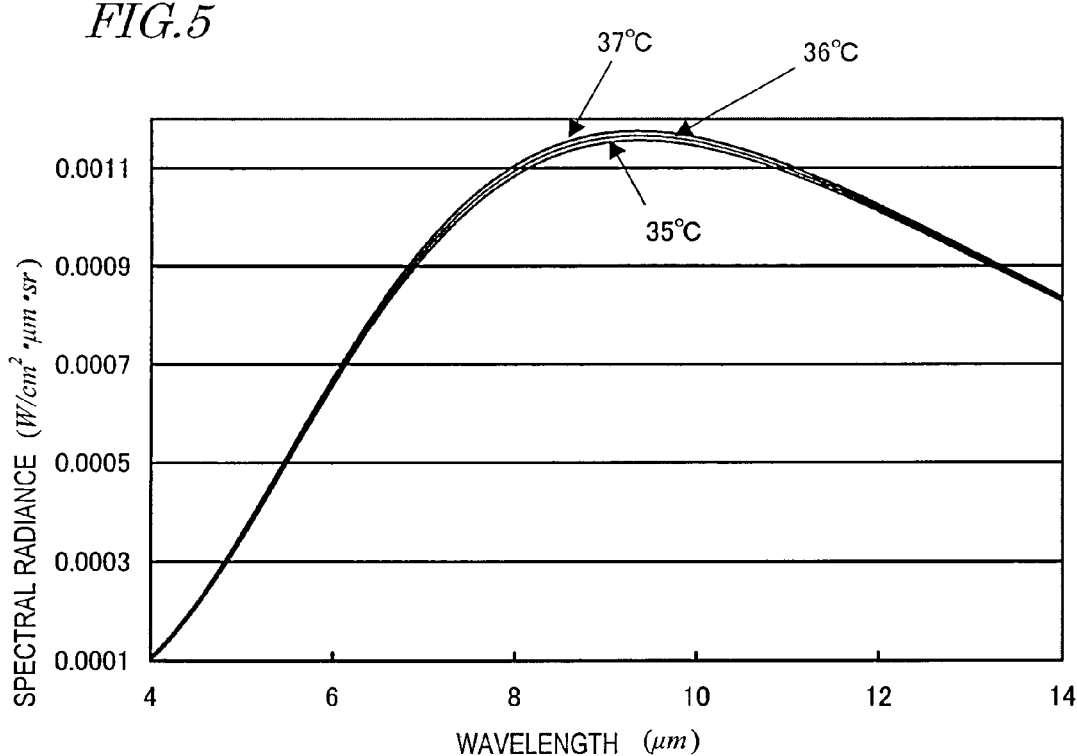
FIG. 5 is a graph including three curves showing the blackbody spectral radiances calculated.

FIG. 5 shows the blackbody spectral radiances of thermal radiations that were calculated when the organism had temperatures of 35° C., 36° C. and 37° C. On the other hand, FIG. 6 shows the absorption spectrum of serum and the spectral radiances of infrared radiations that were emitted as thermal radiations from glucose aqueous solutions with mutually different thicknesses.

It is known that the constituent of the biological constituent and that of serum are similar to each other. That is why in the following example, the absorption spectrum of serum will be used in place of that of the biological constituent. It should be noted that since approximately 70% of an organism's composition is water, which is a major factor that determines the radiation property, calculations were made using an aqueous solution of glucose instead of the organism.

FIG. 5 shows curves representing the spectral radiances that were calculated by substituting 308 K (=35° C.), 309 K (=36° C.) or 310 K (=37° C.) for the organism's temperature T in Equation (2) and that had been converted by dividing the result by pi. On the other hand, FIG. 6 shows curves representing the spectral radiances that were calculated based on the 37° C. curve shown in FIG. 5 and the radiance figured out by Equation (9). The refractive index n and the extinction coefficient k to be substituted into Equation (9) were those of the glucose aqueous solution. The thickness d of the organism that was substituted into Equation (9) and calculated was supposed to fall within the range of 60 µm to 100 µm, which is an average thickness of human eardrum.

As can be seen from FIG. 5, at those temperatures close to the body temperature of an organism, the blackbody emitted infrared radiations, of which the wavelengths were equal to or longer than about 4 µm, as thermal radiations and the spectral radiances reached their maximum values at a wavelength of about 9 µm to about 10 µm. For that reason, in determining the spectral characteristics of the optical filters, a wavelength of at least 4 µm should be selected. It can also be seen that the radiance was affected by the temperature as in Equation (2) at any wavelength.

Figure 6:
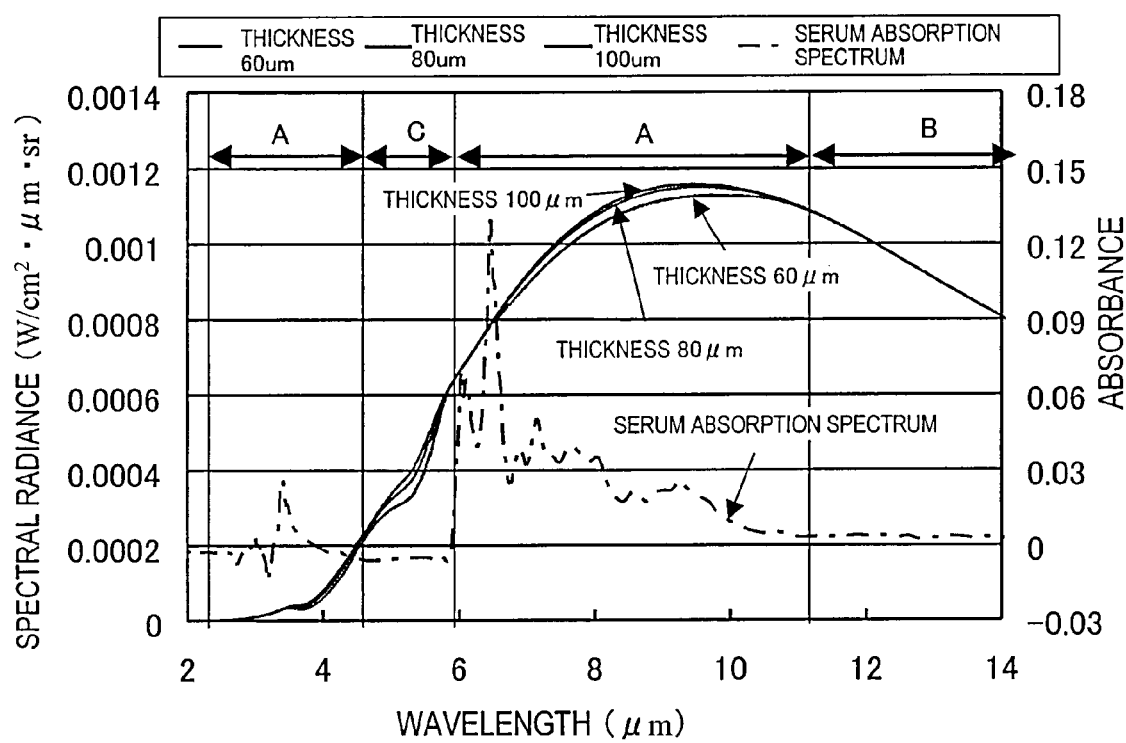
FIG. 6 is a graph including three curves showing the relations between the calculated spectral radiances of infrared radiations emitted from a glucose aqueous solution and the thickness of the glucose aqueous solution and a curve showing a serum absorption spectrum measured.

FIG. 6 shows three different wavelength ranges A, B and C. Specifically, the wavelength range A includes a wavelength at which the infrared radiation changes according to the biological constituent. The wavelength range B includes a wavelength at which the infrared radiation changes according to neither the biological constituent nor the thickness of the object under measurement. And the wavelength range C includes a wavelength at which the infrared radiation changes according to the thickness of the object under measurement, not according to the biological constituent. Since emissivity is equivalent to absorptivity according to Equation (3), the radiance spectrum changes with a variation in the absorption spectrum of serum.

As can be seen from the foregoing description, by selecting an appropriate wavelength from the wavelength range A shown in FIG. 6, the concentration of the object under measurement can be calculated. However, since the radiation spectrum varies with the thickness of the object under measurement in the wavelength range A, the concentration of the object under measurement is preferably calculated with the influence of the thickness of the object under measurement into consideration.

In the wavelength range B shown in FIG. 6, the spectral radiance changes with neither the biological constituent nor the thickness of the object under measurement. That is why the variation in infrared radiation intensity within the wavelength range B corresponds to only a temperature variation. That is to say, by measuring the infrared radiation intensity within the wavelength range B, the temperature can be corrected. And in the wavelength range C shown in FIG. 6, the infrared radiation intensity does not change with the biological constituent but does change with the thickness of the object under measurement. Consequently, a wavelength falling within the wavelength range C may be used to compensate for the influence of the thickness of the object under measurement.

Thus, the third optical filter 123 preferably has such a spectral characteristic as to transmit infrared radiation at a wavelength that is selected from the wavelength range B shown in FIG. 6. And the fourth optical filter 124 preferably has such a spectral characteristic as to transmit infrared radiation at a wavelength that is selected from the wavelength range C shown in FIG. 6.

The third and fourth optical filters 123 and 124 preferably transmit infrared radiations falling within as broad a wavelength range as possible in order to increase the SNR by making greater infrared radiation energy reach the infrared detector 108. For example, the third optical filter 123 is preferably a band-pass filter with a cutoff frequency of about 11 µm to pass wavelengths that are longer than about 11 µm, while the fourth optical filter 124 is preferably a band-pass filter that passes wavelengths falling within the range of about 4.5 µm to about 5.8 µm.

Those optical filters may be made by any known technique, which is not particularly limited herein but may be an evaporation process, for example. Specifically, the optical filters may be fabricated by stacking ZnS, $MgF_2$, PbTe, Ge, ZnSe and/or other layers on a substrate of Si, Ge or ZnSe by an evaporation process or an ion sputtering process, for instance.

In this case, an optical filter with a desired wavelength characteristic can be made by controlling the interference of light in a stack of thin-films with the thicknesses of the respective layers and the order or the number of times the those layers are stacked on the substrate adjusted. For example, the third optical filter 123 may be made in the following manner. First, PbTe may be deposited to about 180 nm on a substrate of Ge and then ZnS and PbTe layers may be alternately stacked thereon to thicknesses of about 800 nm and about 340 nm, respectively, four times by performing an evaporation process. Finally, ZnS is evaporated and deposited thereon once again to about 1700 nm. That is to say, by stacking these ten layers in all, an optical filter that passes wavelengths that are longer than about 11 µm can be obtained.

Figure 7:
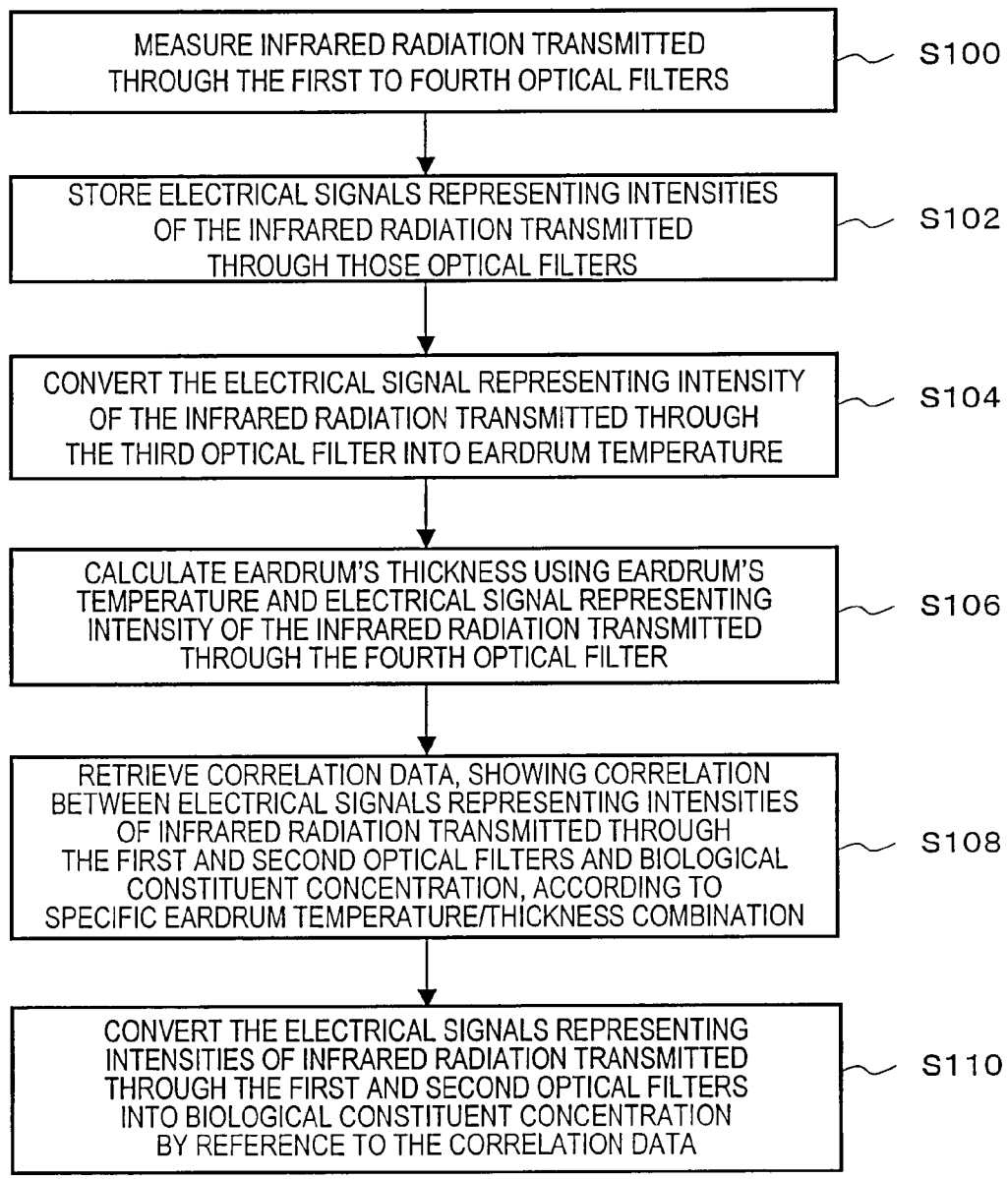
FIG. 7 is a flowchart showing how to counteract the influence of eardrum's temperature and thickness on the infrared radiation intensity measured using the measuring device 100 of the first preferred embodiment.

Hereinafter, the procedure of correcting the infrared radiation intensity with the influence of the eardrum's temperature and thickness taken into consideration will be described with reference to FIG. 7, which is a flowchart showing how to counteract the influence of eardrum's temperature and thickness on the infrared radiation intensity measured with the measuring device 100 of this preferred embodiment.

First, the infrared radiation that have been transmitted through the first, second, third and fourth optical filters 121, 122, 123 and 124 are measured with the infrared detector 108 in Step S100. Next, the values of respective electrical signals representing the intensities of the infrared radiation that have been transmitted through those optical filters are stored in the memory 112 in Step S102.

Figure 8:
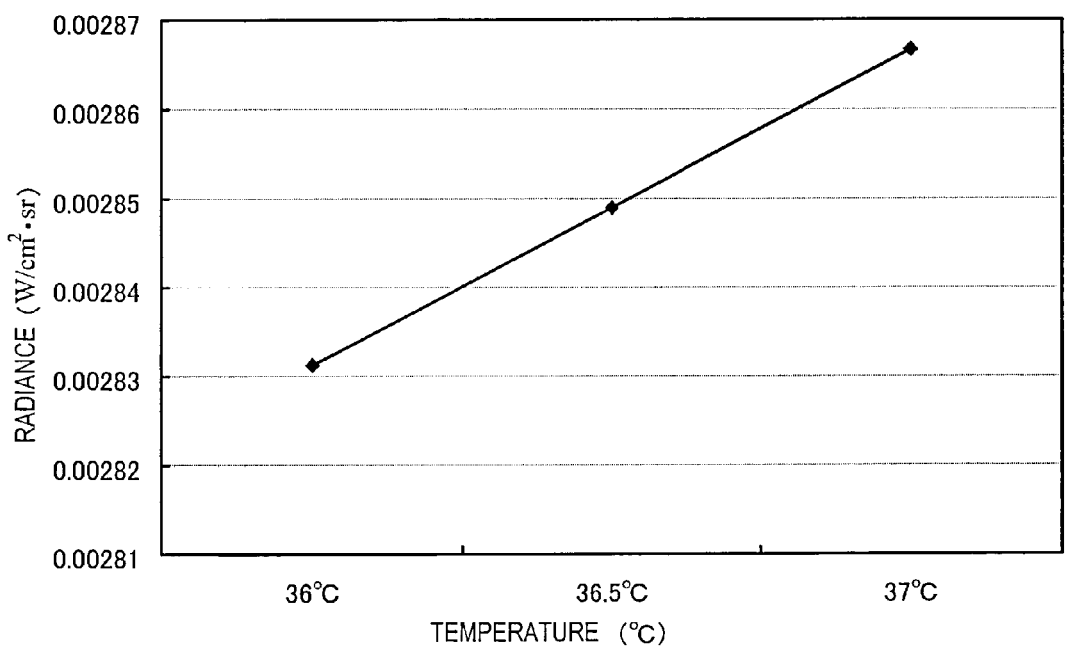
FIG. 8 is a graph showing results of calculations that were made to work out a relation between the radiance of the infrared radiation that was emitted from the glucose aqueous solution and then transmitted through the third optical filter and the temperature of the glucose aqueous solution.

Next, the microcomputer 110 reads the temperature correlation data, showing a correlation between the signal value of the electrical signal representing the intensity of the infrared radiation transmitted through the third optical filter 123 and the eardrum's temperature, from the memory 112. Then, the microcomputer 110 makes reference to the temperature correlation data with the electrical signal B, representing the intensity of the infrared radiation transmitted through the third optical filter 123, as stored in the memory 112, thereby converting the signal value of the electrical signal into the eardrum's temperature in Step S104. An example of the temperature correlation data is shown in FIG. 8, which will be referred to in detail later.

Figure 9:
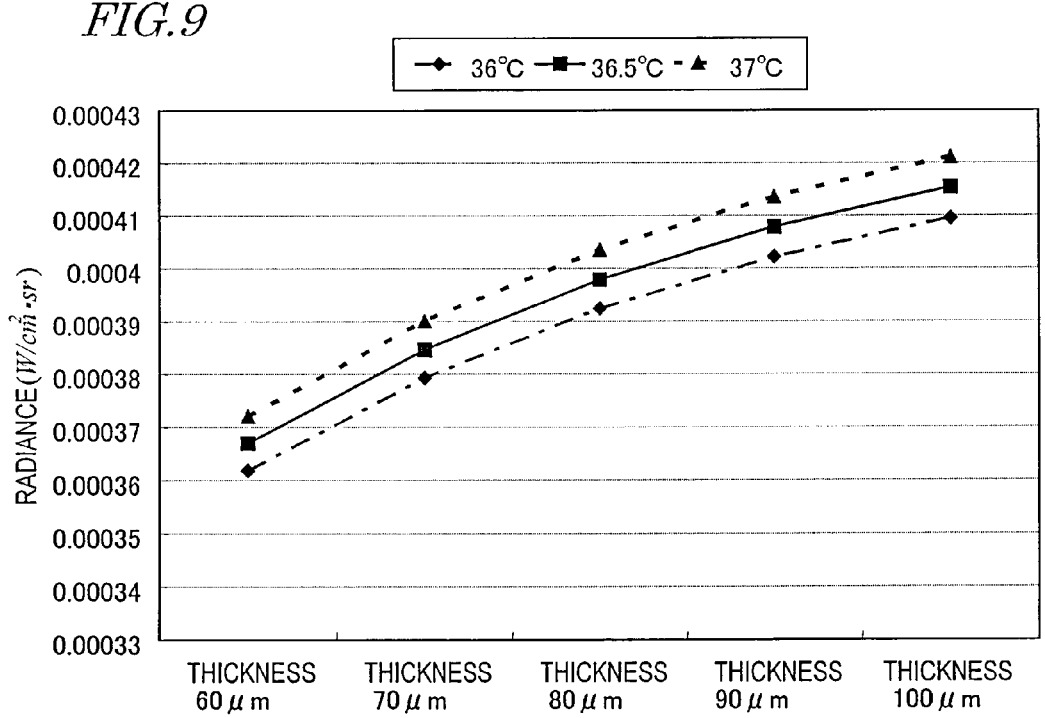
FIG. 9 is a graph showing results of calculations that were made to work out relations between the radiance of the infrared radiation that was emitted from the glucose aqueous solution and then transmitted through the fourth optical filter and the temperatures and thicknesses of the glucose aqueous solution.

Next, the microcomputer 110 reads the thickness correlation data, showing a correlation between the electrical signal representing the intensity of the infrared radiation transmitted through the fourth optical filter 124 and the eardrum's temperature and thickness, from the memory 112. Then, the microcomputer 110 makes reference to the thickness correlation data with the eardrum's temperature that has been detected in Step S104 and the electrical signal C, representing the intensity of the infrared radiation transmitted through the fourth optical filter 124, as stored in the memory 112, thereby figuring out the eardrum's thickness in Step S106. An example of the thickness correlation data is shown in FIG. 9, which will be referred to in detail later.

As for the concentration correlation data showing correlations between the signal values of electrical signals representing the intensities of respective infrared radiation transmitted through the first and second optical filters 121 and 122 and the biological constituent concentration, the same number of different correlation data as that of eardrum's temperature and thickness combinations are stored in the memory 112. For example, if there are three eardrum temperature levels and five eardrum thickness values, 15 different correlation data may be stored.

Subsequently, the microcomputer 110 selectively reads one of multiple concentration correlation data, which is identified by the combination of the eardrum's temperature detected in Step S104 and the eardrum's thickness detected in Step S106, from the memory 112 in Step S108.

Figure 10:
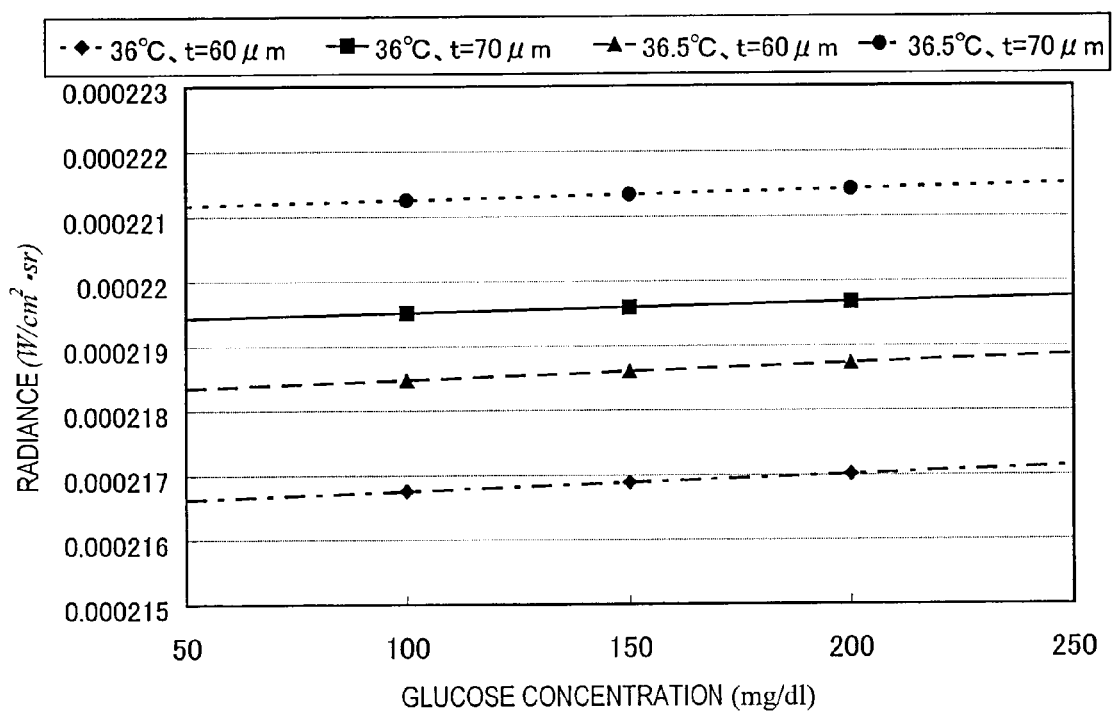
FIG. 10 is a graph showing relations between the radiance of the infrared radiation that was emitted from the glucose aqueous solution and then transmitted through the first optical filter and the concentrations, temperatures and thicknesses of the glucose aqueous solution.

Finally, the microcomputer 110 makes reference to the retrieved concentration correlation data with the electrical signals A1 and A2 representing the intensities of infrared radiation transmitted through the first and second optical filters 121 and 122, respectively as stored in the memory 112, thereby converting the signal values of the electrical signals into a biological constituent concentration in Step S110. An example of the concentration correlation data is shown in FIG. 10, which will be referred to in detail later.

Hereinafter, a specific example of the present invention will be described with reference to FIGS. 8 through 10. In the following example, the first optical filter 121 transmits an infrared radiation with a wavelength of 9.6±0.1 μm, the third optical filter 123 transmits an infrared radiation with a wavelength of 11 μm to 14 μm, and the fourth optical filter 124 transmits an infrared radiation with a wavelength of 4.8 μm to 5.8 μm, an aqueous solution of glucose is used instead of the eardrum, and the first biological constituent as the object of measurement is glucose including no other constituents. Since no biological constituents other than the first biological constituent that is the object of measurement are included in the aqueous solution, the second optical filter 122 is not used in the following example.

FIG. 8 is a graph showing results of calculations that were made to work out a relation between the radiance of the infrared radiation that was emitted as a thermal radiation from the glucose aqueous solution and then transmitted through the third optical filter 123 and the temperature of the glucose aqueous solution. FIG. 9 is a graph showing results of calculations that were made to work out relations between the radiance of the infrared radiation that was emitted as a thermal radiation from the glucose aqueous solution and then transmitted through the fourth optical filter 124 and the temperatures and thicknesses of the glucose aqueous solution. And FIG. 10 is a graph showing relations between the radiance of the infrared radiation that was emitted as a thermal radiation from the glucose aqueous solution and then transmitted through the first optical filter and the concentrations, temperatures and thicknesses of the glucose aqueous solution.

The temperature-radiance relation shown in FIG. 8 is defined as the temperature correlation data. The eardrum thickness-radiance relations for respective temperatures as shown in FIG. 9 are defined as the thickness correlation data. And the concentration-radiance relations for respective temperatures and eardrum thicknesses as shown in FIG. 10 are defined as the temperature correlation data.

For convenience sake, the abscissas of FIGS. 8, 9 and 10 represent the temperature, thickness and concentration, respectively, while the ordinates of all of these three drawings represent the radiance. When actually stored as correlation data in the memory 112, however, electrical signal values representing the respective physical quantities may be retained there. In that case, these data may be stored in the memory 112 either as functions such as those shown in FIGS. 8 through 10 or as tables showing correspondence between the signal values of the respective electrical signals and the biological constituent concentrations.

In FIG. 8, the radiance was calculated by substituting 309K (=36° C.), 309.5K (=36.5° C.) or 310K (=37° C.) as the organism's temperature into Equation (1), dividing the result by pi, and then integrating the results within the wavelength range of 11 μm to 14.3 μm. However, the sensor area included in Equation (1) was not multiplied.

In FIG. 9, the radiance was calculated with the thickness d changed in Equation (9) and substituted into Equation (1). The radiance was also calculated by substituting 309K (=36° C.), 309.5K (=36.5° C.) or 310K (=37° C.) as the temperature in Equation (1) and dividing the result by pi to convert it into radiance. The integration in Equation (1) was performed within the wavelength range of 4.8 μm to 5.8 μm.

In FIG. 10, the radiance was calculated with the thickness d, refractive index corresponding to the glucose concentration and extinction coefficient substituted into Equation (9). The result was then substituted into Equation (1) with 309K (=36° C.) or 309.5K (=36.5° C.) substituted as the temperature into Equation (1). Then, the result was further divided by pi to convert it into radiance. The integration in Equation (1) was performed within the wavelength range of 9.5 μm to 9.7 μm.

First of all, the radiance of the infrared radiation transmitted through the third optical filter 123 does not depend on the thickness of the glucose aqueous solution but changes proportionally to the temperature as shown in FIG. 8. Since the output voltage of the infrared detector 108 is proportional to the radiance of the infrared radiation that has been incident onto the infrared detector 108, the output electrical signal of the infrared detector 108 is also proportional to radiance of the infrared radiation that has been incident onto the infrared detector 108. That is why by reference to the relation between the radiance of the infrared radiation transmitted through the third optical filter 123 and the temperature of the glucose aqueous solution as shown in FIG. 8, the temperature of the glucose aqueous solution can be estimated by the electrical signal representing the infrared radiation that has been transmitted through the third optical filter 123.

Next, as shown in FIG. 9, the radiance of the infrared radiation that has been emitted as a thermal radiation from the glucose aqueous solution and then transmitted through the fourth optical filter 124 depends on the temperature and thickness of the glucose aqueous solution. That is why by reference to the relation shown in FIG. 9 between the radiance of the infrared radiation transmitted through the fourth optical filter 124 and the temperature and thickness of the glucose aqueous solution, the thickness of the glucose aqueous solution can be estimated by the temperature of the glucose aqueous solution and the electrical signal representing the infrared radiation transmitted through the fourth optical filter 124 shown in FIG. 8.

Next, as shown in FIG. 10, the relation between the radiance of the infrared radiation that has been emitted as a thermal radiation from the glucose aqueous solution and then transmitted through the first optical filter and the concentration of the glucose aqueous solution changes with the combination of the temperature and thickness (identified by t in FIG. 10) of the glucose aqueous solution. In FIG. 10, four curves are shown for four different combinations of temperatures and thicknesses of the glucose aqueous solution. That is why an appropriate one may be selected from the four curves shown in FIG. 10 according to the specific combination of the temperature of the glucose aqueous solution shown in FIG. 8 and the thickness of the glucose aqueous solution shown in FIG. 9. And by making reference to the curve selected, the electrical signal representing the infrared radiation that has been transmitted through the first optical filter 121 can be converted into a glucose concentration.

The concentration correlation data stored in the memory 112 to show the correlation between the respective signal values of the electrical signals representing the intensities of the infrared radiations that have been transmitted through the first and second optical filters 121 and 324 and the biological constituent concentration may be acquired in the following manner, for example.

First, as for a patient with a known biological constituent concentration such as a blood glucose level, the infrared radiation that has been emitted as a thermal radiation from his or her eardrum has its intensity measured. In this case, electrical signals representing the intensities of infrared radiations falling within the wavelength ranges to be transmitted by the first and second optical filters 121 and 122 are obtained. By making such measurement on a number of patients with mutually different biological constituent concentrations, eardrum temperatures and eardrum thicknesses, multiple sets of data, each including the electrical signals representing the intensities of infrared radiations falling within the wavelength ranges to be transmitted by the first and second optical filters 121 and 122 and their associated biological constituent concentrations, eardrum temperatures and eardrum thicknesses, can be collected.

Next, by analyzing these data sets that have been collected in this manner, concentration correlation data is obtained. For example, the eardrum temperatures and thicknesses may be graded into multiple levels, and those data sets may be classified according to the eardrum temperature levels and the eardrum thickness levels. For instance, supposing the eardrum temperatures are graded into three different levels and the eardrum thicknesses are graded into five different levels, those data sets are classified into 15 groups. Next, a multivariate analysis is carried out, on a group-by-group basis, by either a multiple regression analysis such as partial least squares regression (PLS) method or a neural network method on the electrical signals representing the intensities of infrared radiations falling within the wavelength ranges to be transmitted by the first and second optical filters 121 and 122 and their associated biological constituent concentrations. As a result, a function showing a correlation between the electrical signals representing the intensities of infrared radiations falling within the wavelength ranges to be transmitted by the first and second optical filters 121 and 122 and their associated biological constituent concentrations can be obtained on a group-by-group basis.

Also, the first optical filter 121 may have such a spectral characteristic as to transmit infrared radiation falling within a measuring wavelength range and the second optical filter 122 may have such a spectral characteristic as to transmit infrared radiation falling within a reference wavelength range. In that case, the difference between the signal values of the electrical signals representing the intensities of infrared radiations falling within the wavelength ranges to be transmitted by the first and second optical filters 121 and 342 may be calculated, and the correlation between that difference and its associated biological constituent concentration may be obtained as the concentration correlation data by performing a linear regression analysis such as a minimum square method, for example.

In the preferred embodiment described above, a method for measuring the eardrum's temperature and thickness using the third and fourth optical filters and for detecting a biological constituent concentration by further using the first and second optical filter is supposed to be adopted. However, any other method may be adopted as well. For example, a function showing a correlation between the electrical signals representing the intensities of infrared radiations falling within the wavelength ranges to be transmitted by the first through fourth optical filters and their associated biological constituent concentrations may be figured out in advance. And the biological constituent concentration may be calculated by substituting the signal values of the respective electrical signals into that function. Alternatively, the function may also be replaced with correlation data in the form of a table showing correspondence between the signal values of those electrical signals and the biological constituent concentrations. If such a method is adopted, that function or table may be stored in the memory 112.

Such a function or such correlation data may be obtained by carrying out a multivariate analysis on the signal values of the electrical signals representing the intensities of infrared radiations falling within the wavelength ranges to be transmitted by the respective optical filters and their associated biological constituent concentrations by either a multiple regression analysis such as the PLS method or a neural network method.

Hereinafter, it will be described how the measuring device 100 operates. In the following description, the user of the measuring device 100 is supposed to measure the concentration of his or her own biological constituent. The same statement will apply to the second and third preferred embodiments of the present invention to be described later.

First, when the user presses the power switch 101 of the measuring device 100, the power is turned ON inside the body 102 to get the measuring device 100 ready to make measurements.

Next, the user holds the body 102 in his or her hand to insert the waveguide 104 into his or her acoustic foramen 200. The waveguide 104 is a conical hollow tube that increases its diameter from the end of the waveguide 104 toward the portion connected to the body 102. That is why the waveguide 104 has such a structure as to prevent itself from being inserted any deeper than the position where the outside diameter of the waveguide 104 gets equal to the inside diameter of the acoustic foramen 200.

Subsequently, when the user presses the measuring start switch 103 of the measuring device 100 at the position where the outside diameter of the waveguide 104 gets equal to the inside diameter of the acoustic foramen 200, the measuring process is started.

On sensing, by reference to the clock signal supplied from the timer 156, that a predetermined amount of time has passed since the measuring process was started, the microcomputer 110 controls the chopper 118 to block the infrared radiation from reaching the optical filter wheel 106. As a result, the measuring process ends automatically. At this point in time, by controlling the display 114 or a buzzer 158, the microcomputer 110 shows a message telling that the measuring process has ended on the display 114, makes the buzzer 158 beep or outputs a voice message or an alarm through a loudspeaker (not shown), thereby notifying the user of the end of the measuring process. On confirming that the measuring process has ended, the user removes the waveguide 104 from his or her acoustic foramen 200.

Then, the microcomputer 110 identifies the electrical signals supplied from the A/D converter 138 on an optical filter basis and calculates the average of the electrical signals for the respective optical filters by the methods described above.

Furthermore, the microcomputer 110 calculates the eardrum's temperature based on the electrical signal associated with the third optical filter 124 and also calculates the eardrum's thickness based on the electrical signal associated with the fourth optical filter 124 by the methods described above.

Next, the microcomputer 110 reads concentration correlation data, associated with the combination of the eardrum's temperature and thickness calculated, from the memory 112, makes reference to the concentration correlation data with the electrical signals representing the intensities of infrared radiations that have been transmitted through the first and second optical filters 121 and 122, and then converts it into a biological constituent concentration, which is presented on the display 114 eventually.

As described above, the measuring device 100 of this preferred embodiment can counteract the influence of the eardrum's temperature and thickness by correcting the temperature and thickness with the electrical signals associated with the third and fourth optical filters 123 and 124, thus achieving higher measuring accuracy.

Embodiment 2

Hereinafter, a biological constituent concentration measuring device according to a second specific preferred embodiment of the present invention will be described with reference to FIGS. 11 and 12.

Figure 11:
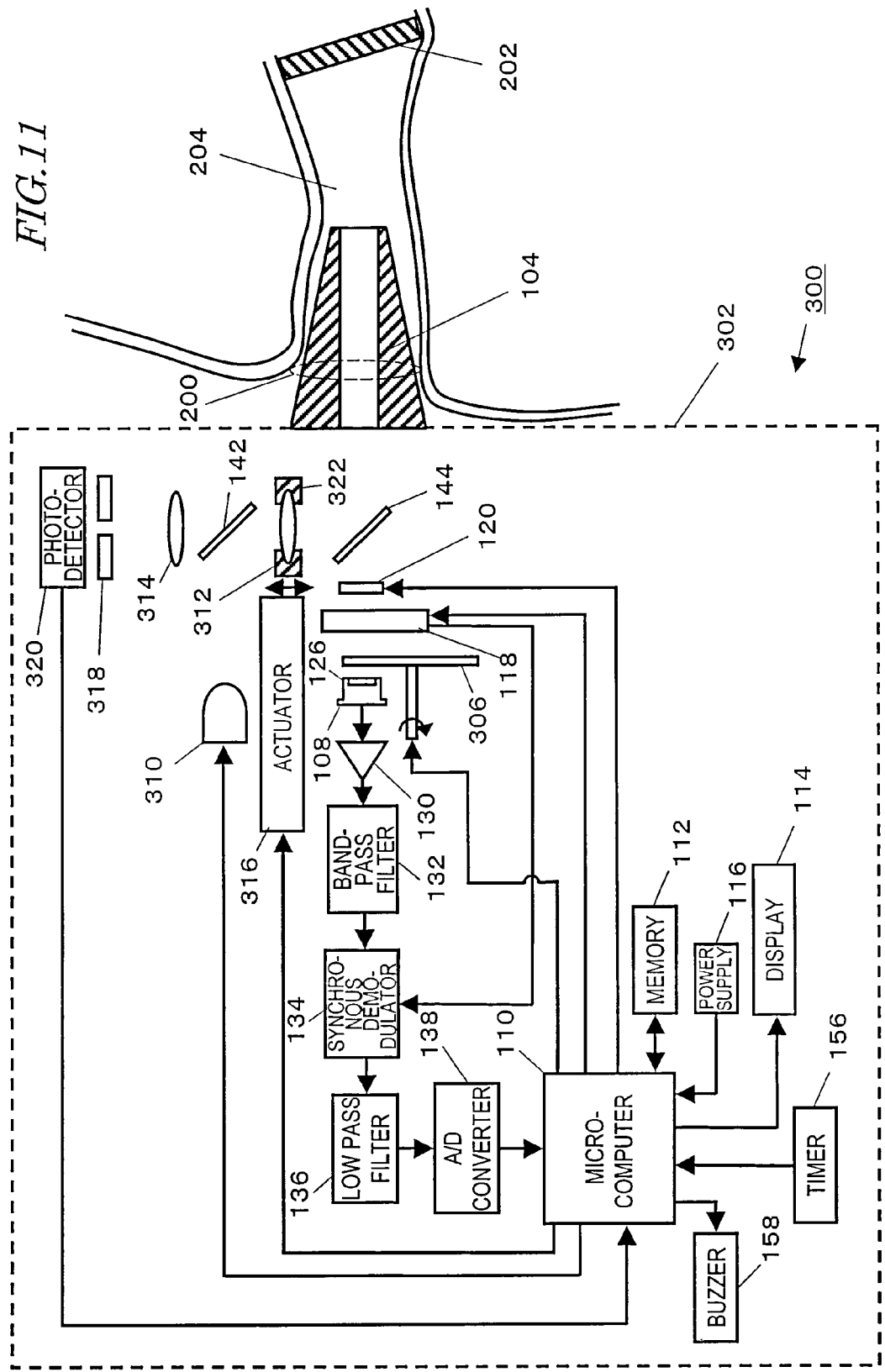
FIG. 11 shows the hardware configuration of a biological constituent concentration measuring device 300 according to a second specific preferred embodiment of the present invention.

FIG. 11 shows the hardware configuration of a biological constituent concentration measuring device 300 (which will be simply referred to herein as "measuring device 300") according to the second preferred embodiment of the present invention. FIG. 12 is a perspective view illustrating the optical filter wheel 306 of the measuring device 300.

Unlike the measuring device 100 of the first preferred embodiment described above, the measuring device 300 has the function of measuring the thickness of an eardrum with a laser beam. To perform this function, the body of the measuring device 300 includes a light source 310, a first condenser lens 312, a second condenser lens 314, an actuator 316, a spatial filter 318, a photodetector 320, a first half mirror 142, and a second half-mirror 144. As there is no need to measure the eardrum's thickness with infrared radiation that has been emitted outside of the eardrum as is done by the measuring device 100 of the first preferred embodiment described above, the optical filter wheel 306 of the second preferred embodiment shown in FIG. 12 does not have a filter corresponding to the fourth optical filter of the first preferred embodiment described above.

In this preferred embodiment, the light source 310, first condenser lens 312, second condenser lens 314, actuator 316, spatial filter 318 and photodetector 320 together function as the acquisition section 12 shown in FIG. 1. Since the other components are the same as the counterparts of the measuring device 100 of the first preferred embodiment, the description thereof will be omitted herein.

The light source 310 emits visible radiation to illuminate the eardrum 202.

Specifically, the light source 310 may be implemented as a laser diode such as a blue laser diode or a red laser diode or a visible radiation source such as an LED. To decrease the depth of focus of the lens, the light source preferably emits a light beam with a short wavelength. Also, to avoid chromatic aberration, a laser radiation source is preferred. A blue laser diode that emits a laser beam with a wavelength falling within the range of 400 nm to 420 nm is preferably used as the light source 310 because the wavelength is short enough and yet chromatic aberration can be avoided in that case.

The visible radiation that has been emitted from the light source 310, reflected by the first half mirror 142, and then condensed by the first condenser lens 312 is reflected by the second half mirror 144 and then guided through the waveguide 104 into an ear canal 204 to illuminate the eardrum 202.

The first half mirror 142 has the function of reflecting a part of visible radiation and transmitting the rest of it.

The second half mirror 144 reflects visible radiation and transmits infrared radiation. The second half mirror 144 is preferably made of a material that does not absorb but transmits infrared radiation and reflects visible radiation, e.g., ZnSe, $CaF_2$, Si or Ge. To transmit the infrared radiation more efficiently, both sides of the second half mirror are preferably coated with antireflection films.

Meanwhile, the visible radiation that has been reflected back from the eardrum 202 by way of the ear canal 204 and then entered the waveguide 104 is reflected by the second half mirror 144, transmitted through the first condenser lens 312, and then is partially transmitted through the first half mirror 142. The visible radiation that has been transmitted through the first half mirror 142 is condensed by the second condenser lens 314 to reach the spatial filter 318. Part of the visible radiation that has been condensed by the second condenser lens 314 and then transmitted through the spatial filter 318 reaches the photodetector 320.

In this preferred embodiment, the spatial filter 318 is formed by cutting a hole with a diameter of about 100 μm through a thin plate of aluminum, iron or any other material that does not transmit visible radiation.

If the first condenser lens 312 is positioned so as to focus the visible radiation either on the surface of the eardrum 202 that is opposed to the ear canal 204 or on the back surface thereof that is opposed to the middle ear, the visible radiation that has been condensed by the second condenser lens 314 will be focused on the hole of the spatial filter 318 and can pass through the spatial filter 318. In that case, the output of the photodetector 320 shows a local maximum. On the other hand, if the first condenser lens 312 is positioned so as not to focus the visible radiation on the surface or the back surface of the eardrum 202, the visible radiation that has been condensed by the second condenser lens 314 will not be focused on the hole of the spatial filter 318 and cannot pass through the spatial filter 318. In that case, the output of the photodetector 320 will decrease.

As the first and second condenser lenses 312 and 314, known lenses may be used. Of these two lenses, the first lens 312 preferably has a large numerical aperture in order to decrease the depth of focus.

The photodetector 320 may be any known one as long as it can detect light having the same wavelength as the light that has been emitted from the light source. For example, a photodiode or a CCD, a CMOS or any other imager may be used. Among other things, if an imager such as a CCD or a CMOS is used as the photodetector 320, measurement and shooting can be done on the eardrum at the same time.

The measuring device 300 has a mechanism for converging the light on the photodetector 320 just as intended by driving the first condenser lens 312 that is held on a lens frame 322.

In response to a control signal supplied from the microcomputer 110, the actuator 316 is driven so as to move the first condenser lens 312 in the optical axis directions (i.e., in the directions pointed by the arrows in FIG. 11). In this case, the position of the first condenser lens 312 is detected by a position sensor (not shown), which provides that information for the microcomputer 110.

Meanwhile, the microcomputer 110 detects the intensity of the output signal of the photodetector 320 and the output of the position sensor, thereby detecting an in-focus position on the eardrum 202. Also, the microcomputer 110 controls the actuator 316 such that the first condenser lens 312 moves to such a position as to maximize the output signal of the photodetector 320.

Thus, even if the distance to the eardrum 202 has varied, the visible radiation that has been reflected from the eardrum 202 can be condensed on the photodetector 320 just as intended.

The actuator 316 and the position sensor may be identical with those used in an autofocusing mechanism for a known camcorder or digital still camera.

For example, the actuator 316 may include a coil attached to the lens frame 322, a yoke secured to the body 302, and a drive magnet attached to the yoke. The lens frame 322 may be supported on two guide poles so as to be movable in the optical axis directions. In that case, when current is supplied to the coil attached to the lens frame 322, driving force that drives the coil in the optical axis directions is generated in the coil located in a magnetic circuit that is formed by the yoke and the drive magnet. As a result, the lens frame 322 moves in the optical axis directions. The direction of the driving force may be controlled so as to be either positive or negative by changing the directions of the current supplied to the coil.

The position sensor may include a sensor magnet, which is magnetized at a certain pitch and attached to the lens frame 322, and a magnetoresistance sensor (which will be referred to herein as an "MR sensor") secured to the body 302, for example. By making the MR sensor secured to the body 302 detect the position of the sensor magnet attached to the lens frame 322, the position of the first condenser lens 312 can be detected.

Figure 12:
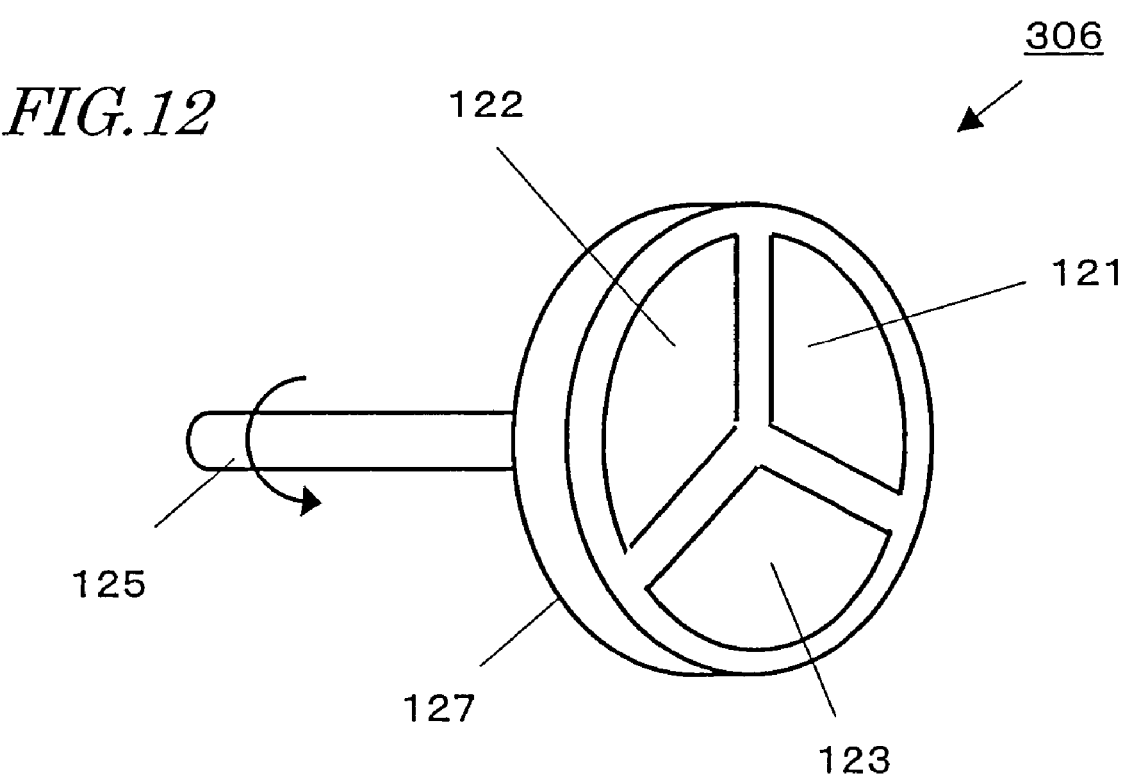
FIG. 12 is a perspective view illustrating an optical filter wheel 306 according to the second preferred embodiment.

As shown in FIG. 12, the optical filter wheel 306 includes a first optical filter 121, a second optical filter 122, a third optical filter 123, and a ring 127 to which these filters are fitted. In the example illustrated in FIG. 12, the first through third optical filters 122 through 123, all of which are fan-shaped, are fitted into the ring 127, thereby forming a disklike member. And at the center of that disklike member, arranged is a shaft 125. The optical properties of these spectral filters are the same as those already described for the first preferred embodiment and the description thereof will be omitted herein. The optical filter wheel 306 functions as a spectral element according to the present invention.

Hereinafter, a method for getting eardrum thickness information, representing the thickness of the eardrum, using the measuring device 300 of this preferred embodiment will be described.

First, the initial position of the first condenser lens 312 is set such that the light condensed by the first condenser lens 312 is focused deeper into the acoustic foramen than the eardrum 202.

Next, the actuator 316 is driven responsive to the control signal supplied from the microcomputer 110, thereby moving the first condenser lens 312 such that the focal point of the first condenser lens 312 shifts from its initial position toward the eardrum 202. In this processing step, the output signal of the photodetector 320 is also monitored as the actuator 316 is driven.

When the output signal of the photodetector 320 reaches a local maximum for the first time (which will be referred to herein as a "first local maximum value"), the visible radiation emitted from the light source 310 is focused on the surface of the eardrum 202 that is opposed to the ear canal 204. The output signal of the position sensor at this point in time is stored in the microcomputer 110 as a signal representing the first position of the lens.

As the actuator 316 is further driven, the output signal of the photodetector 320 once decreases but soon reaches another local maximum (which will be referred to herein as a "second local maximum"). At this point in time, the visible radiation emitted from the light source 310 is condensed on the back surface of the eardrum 202 that is opposed to the middle ear. The output signal of the position sensor at this point in time is stored in the microcomputer 110 as a signal representing the second position of the lens.

Based on the two output signals of the position sensor that have been stored in the microcomputer 110 to represent the first and second positions of the lens, the distance that the first condenser lens 312 travels from the first position to the second position can be calculated. This traveling distance of the first condenser lens 312 represents the thickness of the eardrum 202. By using the traveling distance of the lens, eardrum thickness information, representing the thickness of the eardrum 202, can be obtained.

It should be noted that the thickness of the eardrum 202 could also be measured even without the position sensor. For example, if the position can be determined by the value of the voltage applied to the actuator 316, then the traveling distance can be calculated based on the difference between the voltage values associated with the first and second positions of the lens. This traveling distance corresponds to the thickness of the eardrum 202. Alternatively, if the relation between the variation in the voltage applied to the actuator 316 and the traveling distance is known, then the traveling distance can also be determined by the variation in the voltage applied to move the lens from the first position to the second position.

Figure 13:
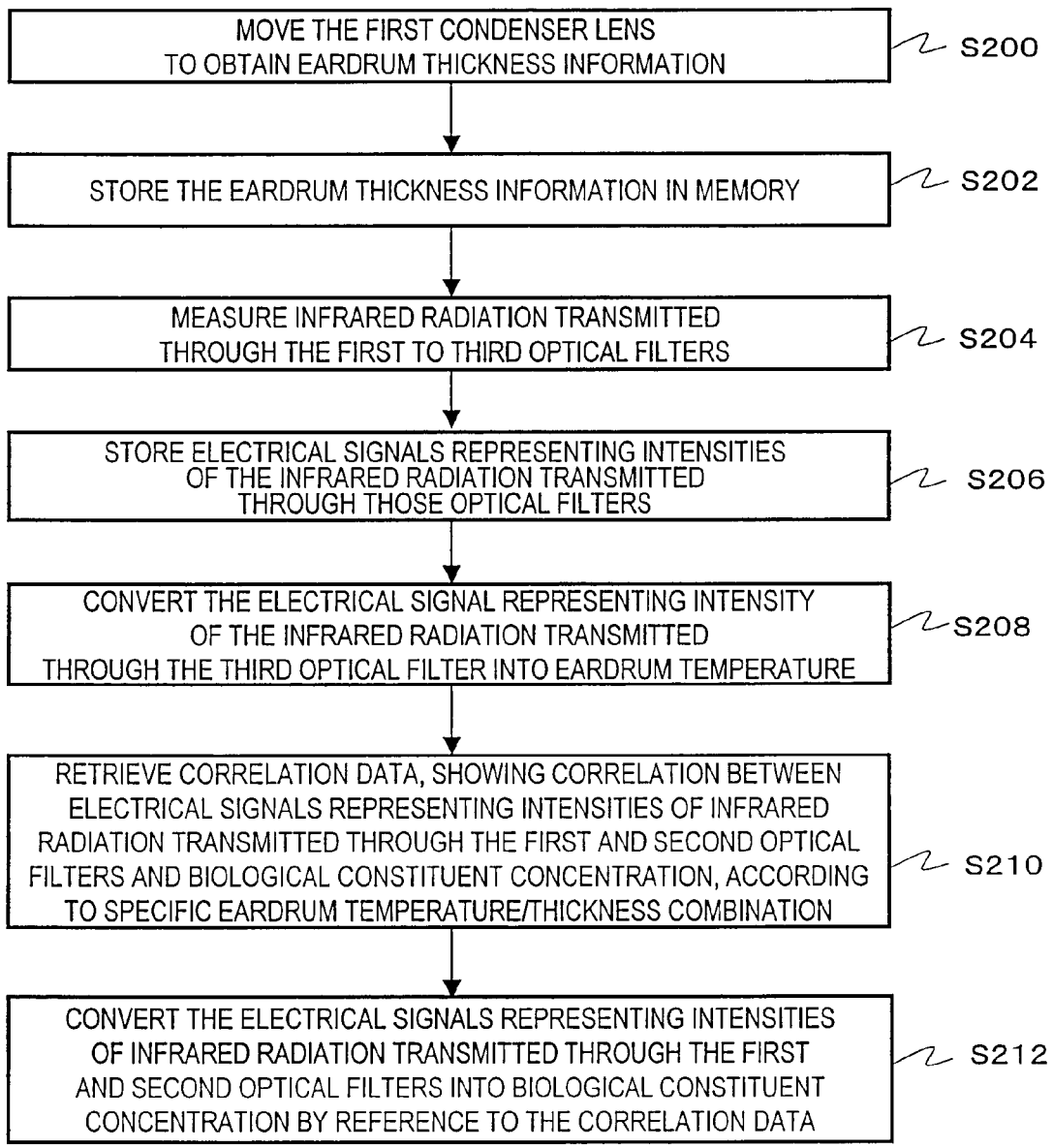
FIG. 13 is a flowchart showing how to counteract the influence of eardrum's temperature and thickness on the infrared radiation intensity measured using the measuring device 300 of the second preferred embodiment.

Hereinafter, the procedure of counteracting the influence of the eardrum's temperature and thickness will be described with reference to FIG. 13, which is a flowchart showing how to counteract the influence of the eardrum's temperature and thickness on the intensity of the infrared radiation that has been measured with the measuring device 300 of this preferred embodiment.

First, by moving the first condenser lens 312 using the actuator 316, eardrum thickness information, representing the thickness of the eardrum 202, is obtained in Step S200 by the method described above and then the output signal of the position sensor, representing the eardrum thickness information, is stored in the memory 112 in Step S202.

Next, infrared radiation that have been transmitted through the first, second and third optical filters 121, 122 and 123 are detected by the infrared detector 108 in Step S204. The electrical signals representing the intensities of the infrared radiation that have been transmitted through these optical filters are stored in the memory 112 in Step S206.

Next, the microcomputer 110 reads the correlation data, showing a correlation between the electrical signal representing the intensity of the infrared radiation transmitted through the third optical filter 123 and the eardrum's temperature, from the memory 112. Then, the microcomputer 110 makes reference to the correlation data, thereby converting the electrical signal, representing the intensity of the infrared radiation transmitted through the third optical filter 123, as stored in the memory 112 into the eardrum's temperature in Step S208.

As for the correlation data showing correlations between the electrical signals representing the intensities of respective infrared radiation transmitted through the first and second optical filters 121 and 122 and the biological constituent concentration, the same number of different correlation data as that of different combinations of output signals of the position sensor, representing eardrum's temperatures and thicknesses, are stored in the memory 112. For example, if there are three eardrum temperature levels and five eardrum thickness values, 15 different correlation data may be stored.

Subsequently, the microcomputer 110 selectively reads one of multiple correlation data, which is identified by the combination of the eardrum's temperature detected in Step S208 and the eardrum's thickness information obtained in Step S200, from the memory 112 in Step S210.

Finally, the microcomputer 110 makes reference to the retrieved correlation data, thereby converting the electrical signals representing the intensities of infrared radiation transmitted through the first and second optical filters 121 and 122 as stored in the memory 112 into a biological constituent concentration in Step S212.

Hereinafter, it will be described how the measuring device 300 of this preferred embodiment operates. The measuring device 400 operates in quite the same way as the measuring device 100 of the first preferred embodiment described above after its power has been turned ON and until the waveguide is inserted into the ear, and the description thereof will be omitted herein.

Subsequently, when the user presses the measuring start switch 103 of the measuring device 300 while holding the measuring device 300 at the position where the outside diameter of the waveguide 104 gets equal to the inside diameter of the acoustic foramen 200, the microcomputer 110 measures the thickness of the eardrum based on the respective output signals of the photodetector 320 and the position sensor by the method described above to obtain eardrum thickness information.

On determining that the eardrum thickness information has been obtained, the microcomputer 110 begins measuring the infrared radiation next.

On sensing, by reference to the clock signal supplied from the timer 156, that a predetermined amount of time has passed since the measuring process was started, the microcomputer 110 controls the chopper 118 to block the infrared radiation from reaching the optical filter wheel 306. As a result, the measuring process ends automatically. At this point in time, by controlling the display 114 or the buzzer 158, the microcomputer 110 shows a message telling that the measuring process has ended on the display 114, makes the buzzer 158 beep or outputs a voice message or an alarm through a loudspeaker (not shown), thereby notifying the user of the end of the measuring process. On confirming that the measuring process has ended, the user removes the waveguide 104 from his or her acoustic foramen 200.

Then, the microcomputer 110 identifies the electrical signals supplied from the A/D converter 138 on an optical filter basis and calculates the average of the electrical signals for the respective optical filters by the methods described above.

Furthermore, the microcomputer 110 calculates the eardrum's temperature based on the electrical signal associated with the third optical filter 124 by the method described above.

Next, the microcomputer 110 reads correlation data, showing correlation between the electrical signals representing the intensities of the infrared radiations that have been transmitted through the first and second optical filters 121 and 122 and the biological constituent concentration for the specific combination of the eardrum's temperature and thickness calculated, from the memory 112, and converts, by reference to this correlation data, the electrical signals representing the intensities of infrared radiations that have been transmitted through the first and second optical filters 121 and 122 into a biological constituent concentration, which is then presented on the display 114 eventually.

As described above, the measuring device 300 of this preferred embodiment can counteract the influence of the eardrum's temperature and thickness by correcting the temperature and thickness, thus achieving higher measuring accuracy.

Embodiment 3

Figure 14:
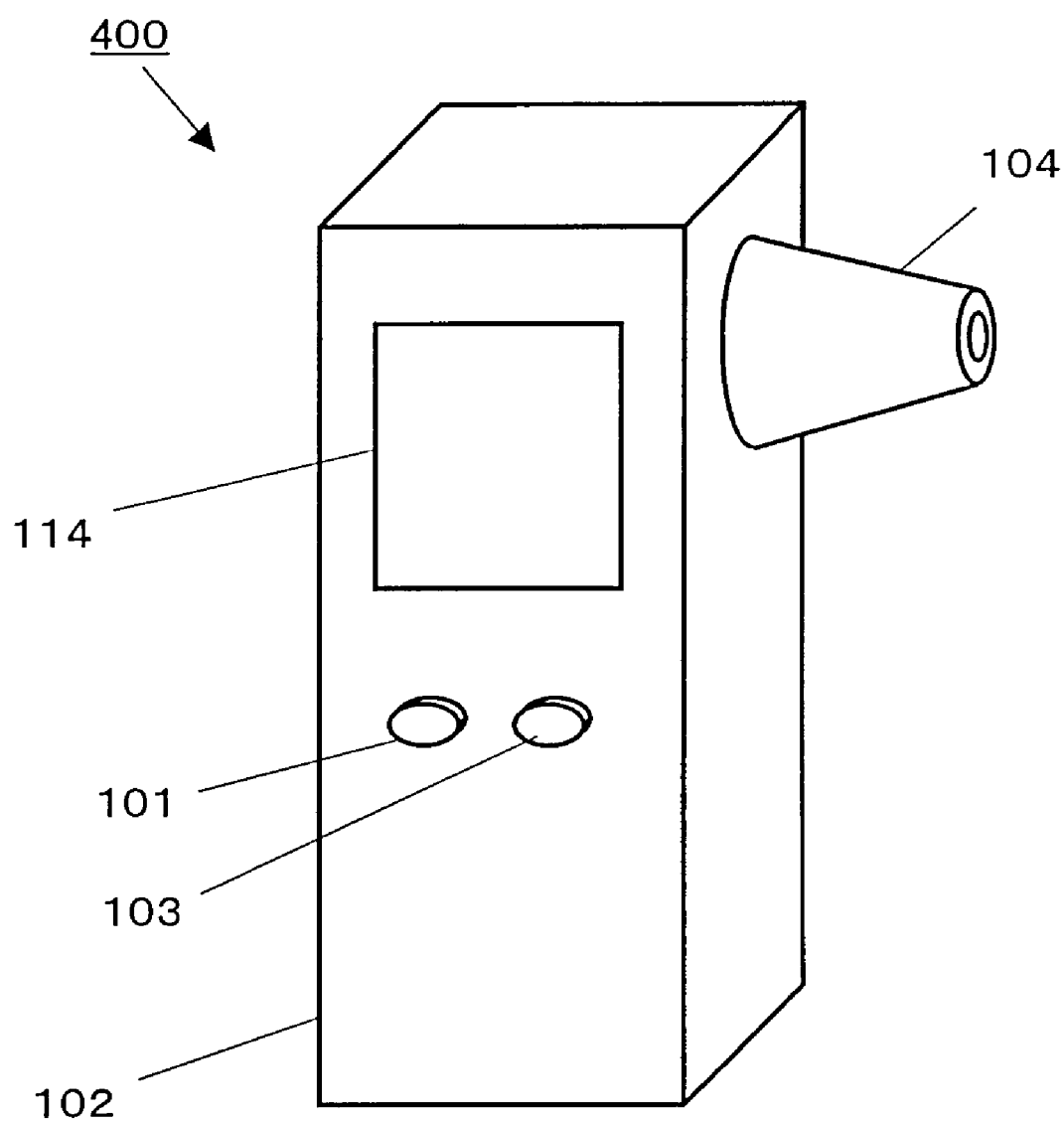
FIG. 14 is a perspective view illustrating the appearance of a biological constituent concentration measuring device 400 according to a third specific preferred embodiment of the present invention.

FIG. 14 is a perspective view illustrating the appearance of a biological constituent concentration measuring device 400 (which will be simply referred to herein as an "measuring device 400") according to a third specific preferred embodiment of the present invention. As the appearance of this measuring device is substantially the same as that illustrated in FIG. 1, the description thereof will be omitted herein.

Hereinafter, the internal configuration of the body of the measuring device 400 will be described with reference to FIG. 15, which shows the hardware configuration of the measuring device 400.

Unlike the measuring device 100 of the first preferred embodiment described above, the measuring device 400 has the function of increasing the intensity of the infrared radiation that has been emitted from the eardrum. To perform this function, the body of the measuring device 400 includes an infrared radiation source 700 for emitting an infrared radiation and a half mirror 702. In the other respects, the measuring device 400 has quite the same configuration as the measuring device 100 of the first preferred embodiment described above, and the description thereof will be omitted herein.

The infrared radiation source 700 emits infrared radiation to irradiate the eardrum 202. The infrared radiation that has been emitted from the infrared radiation source 700 and then reflected from the half mirror 702 is guided through the waveguide 104 to enter the ear canal 204 and irradiate the eardrum 202. The infrared radiation that has reached the eardrum 202 is reflected from the eardrum 202 back toward the measuring device 400. This infrared radiation is guided through the waveguide 104, transmitted through the half mirror 702 and the optical filter wheel 106, and then detected at the infrared detector 108.

The intensity of the light reflected from the eardrum 202 and then detected by the measuring device 400 is calculated as the product of the reflectance given by Equation (8) and the intensity of the infrared radiation impinging on the eardrum 202. As can be seen from Equation (8), as the biological constituent changes its concentrations, the refractive index and the extinction coefficient of the organism change. The reflectance is normally as small as about 0.03 in the infrared range of the spectrum and depends very little on the refractive index and the extinction coefficient as can be seen from Equation (8). The reflectance hardly varies even when the biological constituent changes its concentrations. However, if the intensity of the infrared radiation emitted from the infrared radiation source 700 is increased, the variation in reflectance can be sensed highly accurately. It should be noted that if an object such as the eardrum 202, of which the thickness is several times as large as the wavelength, is irradiated with an infrared radiation with high intensity and if its reflected light is measured, the degree of interference of light changes with the thickness of the eardrum 202. As a result, the intensity of the reflected light changes.

As the infrared radiation source 700, any known light source may be used without restriction. For example, a silicon carbide light source, a ceramic light source, an infrared LED, or a quantum cascade laser may be used. Any of these light sources may be selectively used according to the wavelength range required. As for an infrared LED, for instance, a single light source may be provided for each wavelength required.

The half mirror 702 has the function of splitting an infrared radiation into two bundles of rays. The third half mirror 702 may be made of ZnSe, $CaF_2$, Si, Ge or any other suitable material. Furthermore, to control the transmittance and reflectance of the infrared radiation, the half mirror 702 is preferably coated with an antireflection film.

The memory 112 stores the temperature correlation data showing a correlation between the signal value of the electrical signal representing the intensity of the infrared radiation transmitted through the third optical filter 123 and the eardrum's temperature, the thickness correlation data showing a correlation between the signal value of the electrical signal representing the intensity of the infrared radiation transmitted through the fourth optical filter 124 and the eardrum's temperature and thickness, and the concentration correlation data showing correlations between the respective signal values of the electrical signals representing the intensities of the infrared radiation transmitted through the first and second optical filters 121 and 122 and the biological constituent concentration.

The temperature correlation data and the thickness correlation data may be the same as those used for the first preferred embodiment described above.

As for the concentration correlation data, the same number of different correlation data as that of eardrum's temperature and thickness combinations are stored in the memory 112. For example, if there are three eardrum temperature levels and five eardrum thickness values, 15 different correlation data may be stored. These correlation data may be collected in the following manner, for example.

First, as for a patient with a known biological constituent concentration such as a blood glucose level, the infrared radiation that has been emitted from the infrared radiation source 700 toward, and then reflected from, his or her eardrum has its intensity measured. In this case, electrical signals representing the intensities of infrared radiations falling within the wavelength ranges to be transmitted by the first and second optical filters 121 and 122 are obtained. By making such measurement on a number of patients with mutually different biological constituent concentrations, eardrum temperatures and eardrum thicknesses, multiple sets of data, each including the electrical signals representing the intensities of infrared radiations falling within the wavelength ranges to be transmitted by the first and second optical filters 121 and 122 and their associated biological constituent concentrations, eardrum temperatures and eardrum thicknesses, can be collected.

Next, by analyzing these data sets that have been collected in this manner as is done in the first preferred embodiment described above, correlation data is obtained. For example, the eardrum temperatures and thicknesses may be graded into multiple levels, and those data sets may be classified according to the eardrum temperature levels and the eardrum thickness levels. For instance, supposing the eardrum temperatures are graded into three different levels and the eardrum thicknesses are graded into five different levels, those data sets are classified into 15 groups. Next, a multivariate analysis is carried out, on a group-by-group basis, by either a multiple regression analysis such as partial least squares regression (PLS) method or a neural network method on the electrical signals representing the intensities of infrared radiations falling within the wavelength ranges to be transmitted by the first and second optical filters 121 and 122 and their associated biological constituent concentrations. As a result, a function showing a correlation between the electrical signals representing the intensities of infrared radiations falling within the wavelength ranges to be transmitted by the first and second optical filters 121 and 122 and their associated biological constituent concentrations can be obtained on a group-by-group basis.

By detecting the infrared radiation that has been emitted from the infrared radiation source 700 toward, and then reflected from, the eardrum, the biological constituent concentration can be measured.

Hereinafter, it will be described how the measuring device 400 of this preferred embodiment operates. The measuring device 400 operates in quite the same way as the measuring device 100 of the first preferred embodiment described above after its power has been turned ON and until the waveguide is inserted into the ear, and the description thereof will be omitted herein.

Subsequently, when the user presses the measuring start switch 103 of the measuring device 100 while holding the measuring device 100 at the position where the outside diameter of the waveguide 104 gets equal to the inside diameter of the acoustic foramen 200, the measuring process starts.

First, while the infrared radiation source 700 is still not activated yet, the infrared radiation that has been emitted as a thermal radiation from the eardrum 202 is measured. Next, on sensing, by reference to the clock signal supplied from the timer 156, that a predetermined amount of time has passed since the measuring process was started, the microcomputer 110 activates the infrared radiation source 700. As a result, not only the infrared radiation that has been emitted as a thermal radiation from the eardrum 202 but also the infrared radiation that has been emitted from the infrared radiation source 700 toward, and then reflected from, the eardrum are measured.

On sensing, by reference to the clock signal supplied from the timer 156, that a predetermined amount of time has passed since the measuring process was started, the microcomputer 110 controls the infrared radiation source 700 to shield the infrared radiation. As a result, the measuring process ends automatically. At this point in time, by controlling the display 114 or the buzzer 158, the microcomputer 110 shows a message telling that the measuring process has ended on the display 114, makes the buzzer 158 beep or outputs a voice message or an alarm through a loudspeaker (not shown), thereby notifying the user of the end of the measuring process. On confirming that the measuring process has ended, the user removes the waveguide 104 from his or her acoustic foramen 200.

Then, the microcomputer 110 identifies the electrical signals supplied from the A/D converter 138 on an optical filter basis and calculates the average of the electrical signals for the respective optical filters by the methods described above.

Furthermore, the microcomputer 110 calculates the eardrum's temperature based on the electrical signal associated with the third optical filter 124 and detected while the infrared radiation source 700 was not activated yet and also calculates the eardrum's thickness based on the electrical signal associated with the fourth optical filter 124 and detected while the infrared radiation source 700 was not activated yet.

Next, the microcomputer 110 reads correlation data, showing correlation between the electrical signals representing the intensities of the infrared radiations that have been transmitted through the first and second optical filters 121 and 122 and the biological constituent concentration for the specific combination of the eardrum's temperature and thickness calculated, from the memory 112, and converts, by reference to this correlation data, the electrical signals representing the intensities of infrared radiations that have been transmitted through the first and second optical filters 121 and 122 while the infrared radiation source 700 is activated into a biological constituent concentration, which is eventually presented on the display 114.

In the preferred embodiment described above, an optical filter wheel is supposed to be used as a spectral element. However, any other spectral element may be used as long as the element can split an infrared radiation into multiple rays with mutually different wavelengths. For example, a Michelson interferometer or a diffraction grating for transmitting an infrared radiation falling within a particular wavelength range may be used. Besides, there is no need to integrate a number of filters together as in the optical filter wheel. Furthermore, when an infrared radiation source such as an infrared LED or a quantum cascade laser that can emit a radiation with a particular wavelength is used, there is no need to split the infrared radiation. In that case, the first and second optical filters provided for the optical filter wheel of the preferred embodiment described above are no longer necessary.

As described above, the biological constituent concentration measuring device of this preferred embodiment can counteract the influence of the eardrum's temperature and thickness by using the electrical signals associated with the third and fourth optical filters, thus achieving higher measuring accuracy.

INDUSTRIAL APPLICABILITY

A biological constituent concentration measuring device according to the present invention can be used effectively to measure a biological constituent concentration non-invasively, e.g., measure a glucose concentration without collecting blood.

The invention claimed is:

1. A device for measuring the concentration of a biological constituent, the device comprising:
   a detecting section for detecting infrared radiation emitted by an eardrum;
   an acquisition section for acquiring thickness information representing the thickness of the eardrum; and
   a computing section for calculating the concentration of the biological constituent based on the infrared radiation detected and the thickness information acquired.

2. The device of claim 1, wherein on receiving an infrared radiation falling within a wavelength range A1, including the wavelength of an infrared radiation absorbed into the biological constituent, the detecting section outputs a signal A1 representing the intensity of the infrared radiation,
   on receiving an infrared radiation falling within a wavelength range B, which is selected from a wavelength range that is equal to or longer than 11 μm, the detecting section outputs a signal B representing the intensity of the infrared radiation, and
   on receiving an infrared radiation falling within a wavelength range C, which is selected from the wavelength range of 4.5 μm to 5.8 μm, the detecting section outputs a signal C representing the intensity of the infrared radiation, and
   wherein the computing section calculates the concentration of the biological constituent based on the signals A1, B and C that have been supplied from the detecting section.

3. The device of claim 2, wherein on receiving an infrared radiation that falls within a wavelength range A2, in which the infrared radiation is absorbed into the biological constituent less than the infrared radiation falling within the wavelength range A1, and that is absorbed into a different biological constituent than the biological constituent, the detecting section outputs a signal A2 representing the intensity of the infrared radiation, and
   wherein the computing section calculates the concentration of the biological constituent based on the signals A1, A2, B and C that have been supplied from the detecting section.

4. The device of claim 2, further comprising a storage section for storing concentration correlation data showing a correlation between respective signal values of the detecting section about the wavelength ranges A1, B and C and the concentration of the biological constituent, and
   wherein the computing section calculates the concentration of the biological constituent by making reference to the correlation data with the signals A1, B and C that have been supplied from the detecting section.

5. The device of claim 4, wherein the storage section further stores temperature correlation data showing a correlation between the signal value of the detecting section about the wavelength range B and a temperature and thickness correlation data showing a correlation between the temperature and the signal value of the detecting section about the wavelength range C, and the thickness of the eardrum, and
   wherein the acquisition section determines the temperature by reference to the temperature correlation data with the signal B supplied from the detecting section and then acquires the thickness information by the reference to the thickness correlation data with the temperature determined and the signal C supplied from the detecting section.

6. The device of claim 5, wherein the computing section calculates the concentration of the biological constituent based on the concentration correlation data with the temperature determined, the thickness information acquired, and the signal value of the detecting section about the wavelength range A1.

7. The device of claim 2, further comprising at least three optical elements that are adapted to be arranged on an optical path between the eardrum and the detecting section, the optical elements including an optical element that transmits the infrared radiation falling within the wavelength range A1, an optical element that transmits the infrared radiation falling within the wavelength range B, and an optical element that transmits the infrared radiation falling within the wavelength range C.

8. The device of claim 1, further comprising:
   a light source for emitting light;
   a lens for condensing the light that has been emitted from the light source and then reflecting from the eardrum;
   an actuator for moving the lens;
   a spatial filter; and
   a photodetector for detecting a portion of the light that has been condensed by the lens and then transmitted through the spatial filter and outputting a signal representing the intensity of the light,
   wherein the acquisition section monitors the levels of the output signal of the photodetector with the lens moved, and calculates, as the thickness information, a distance that the lens travels from a first position where the output signal of the photodetector shows a first local maximum value to a second position where the output signal of the photodetector shows a second local maximum value.

9. the device of claim 8, wherein the light source is a laser radiation source that emits a laser beam with a wavelength falling within the range of 400 nm to 420 nm.

10. The device of claim 8, wherein on receiving an infrared radiation falling within a wavelength range A1, including the wavelength of an infrared radiation absorbed into the biological constituent, the detecting section outputs a signal A1 representing the intensity of the infrared radiation, and on receiving an infrared radiation falling within a wavelength range B, which is equal to or longer than 11 μm, the detecting section outputs a signal B representing the intensity of the infrared radiation, and wherein the computing section calculates the concentration of the biological constituent based on the signals A1 and B that have been supplied from the detecting section.

11. The device of claim 10, further comprising a storage section for storing correlation data showing a correlation between respective signal values of the detecting section about the wavelength ranges A1 and B, the thickness information, and the concentration of the biological constituent, and wherein the computing section calculates the concentration of the biological constituent by reference to the correlation data with the signals A1 and B that have been supplied from the detecting section and with the thickness information.

12. The device of claim 1, further comprising:

a light source for emitting light;

an optical system for converging the light onto the eardrum; and a photodetector for detecting the light that has been reflected from the eardrum, wherein the acquisition section calculates the thickness information based on a first setting of the optical system when the light emitted from the light source is focused on a first side of the eardrum and a second setting of the optical system when the light emitted from the light source is focused on a second side of the eardrum.

13. The device of claim 1, further comprising an infrared radiation source for increasing the intensity of the infrared radiation emitted by the eardrum, wherein the detecting section outputs a signal representing the intensity of the infrared radiation received.

14. The device of claim 1, wherein the acquisition section acquires the thickness information over a network.

15. The device of claim 1, wherein the acquisition section acquires the thickness information by way of a removable storage medium.

16. The device of claim 1, further comprising an output section for outputting information about the biological constituent concentration calculated.

* * * * *

UNITED STATES PATENT AND TRADEMARK OFFICE
CERTIFICATE OF CORRECTION

PATENT NO. : 7,684,841 B2
APPLICATION NO. : 11/915889
DATED : March 23, 2010
INVENTOR(S) : Masahiko Shioi It is certified that error appears in the above-identified patent and that said Letters Patent is hereby corrected as shown below:

Column 28, line 28, "by the reference" should read -- by reference --;

line 50, "then reflecting" should read -- then reflected --; and line 65, "the device" should read -- The device --.

Signed and Sealed this

Thirteenth Day of July, 2010

David J. Kappos
*Director of the United States Patent and Trademark Office*